US006875846B2

(12) United States Patent
Rennert et al.

(10) Patent No.: US 6,875,846 B2
(45) Date of Patent: Apr. 5, 2005

(54) HETEROLOGOUS POLYPEPTIDE OF THE TNF FAMILY

(75) Inventors: Paul Rennert, Millis, MA (US); Jeffrey S. Thompson, Stoneham, MA (US); Christine Ambrose, Reading, MA (US); Teresa G. Cachero, Brookline, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 84 days.

(21) Appl. No.: 10/214,065

(22) Filed: Aug. 7, 2002

(65) Prior Publication Data

US 2003/0023038 A1 Jan. 30, 2003

Related U.S. Application Data

(63) Continuation of application No. PCT/US01/04121, filed on Feb. 8, 2001
(60) Provisional application No. 60/181,670, filed on Feb. 11, 2000.

(51) Int. Cl.$^7$ .......................... C07K 14/52; C07H 21/04
(52) U.S. Cl. ....................................... 530/351; 536/23.5
(58) Field of Search .......................... 530/351; 536/23.5

(56) References Cited

U.S. PATENT DOCUMENTS

| 5,194,596 | A | * | 3/1993 | Tischer et al. | ............... | 530/399 |
| 5,350,836 | A | * | 9/1994 | Kopchick et al. | ........... | 530/399 |
| 5,489,519 | A | | 2/1996 | Deeley et al. | ............. | 435/69.1 |
| 2003/0223996 | A1 | * | 12/2003 | Ruben et al. | ............. | 424/146.1 |

FOREIGN PATENT DOCUMENTS

| EP | 0120694 B2 | 10/1984 |
| EP | 0125023 A1 | 11/1984 |
| EP | 0171496 B1 | 2/1986 |
| EP | 0173494 A2 | 3/1986 |
| EP | 0239400 B1 | 9/1987 |
| WO | WO 86/01533 | 3/1986 |
| WO | WO 90/07861 | 7/1990 |
| WO | WO 91/09967 | 7/1991 |
| WO | WO 97/33902 | 9/1997 |
| WO | WO 98/18921 | 5/1998 |
| WO | WO 98/27114 | 6/1998 |
| WO | WO 99/12964 | 3/1999 |
| WO | WO 99/12965 | 3/1999 |
| WO | WO 99/50416 | 10/1999 |
| WO | WO 00/50597 | 8/2000 |

OTHER PUBLICATIONS

Aggarwal and Natarajan, "Tumor necrosis factors: developments during the last decade," *Eur Cytokine Netw*, 7, 1996, pp. 93–124.
Beutler, "The role of tumor necrosis factor in health and disease," *J. Rheumatol*, 26, Suppl 57, 1999, pp. 16–21.
Browning et al., "Signaling through the lymphotoxin beta receptor induces the death of some adenocarcinoma tumor lines," *J Exp Med*, 183, 1996, pp. 867–878.
Chicheportiche et al., "TWEAK, a new secreted ligand in the tumor necrosis factor family that weakly induces apoptosis," *J Biol Chem*, 272, 1997, pp. 32401–32410.

Gura, "How TRAIL kills cancer cells, but not normal cells," *Science*, 277, 1997, pp. 768.
Hahne et al., "APRIL, a new ligand of the tumor necrosis factor family, stimulates tumor cell growth," *J Exp Med*, 188, 1998, pp. 1185–1190.
Jiang et al., "Cell cycle gene expression and E2F transcription factor complexes in human melanoma cells induced to terminally differentiate," *Oncogene*, 11, 1995, pp. 1179–1189.
Karlin and Altschul, "Methods for assessing the statistical significance of molecular sequence features by using general scoring schemes," *Proc Natl Acad Sci*, USA 87, 1990, pp. 2264–2268.
Karlin and Altschul, "Applications and statistics for multiple high–scoring segments in molecular sequences," *Proc Natl Acad Sci*, USA 90, 1993, pp. 5873–5877.
Kelly et al., "APRIL/trdl–1, a tumor necrosis factor–like ligand, stimulates cell death," *Can Res*, 60, 2000, pp. 1021–1027.
Lockhart et al., "Expression monitoring by hybridization to high–density oligonucleotide arrays," *Nat Biotechnol*, 14, 1996, pp. 1675–1680.
MacKay et al., "Lymphotoxin β receptor triggering induces activation of the nuclear factor kB transcriptin factor in some cell types," *J Biol Chem*, 271, 1996, pp. 24934–24938.
MacKay et al., "Both the lymphotoxin and tumor necrosis factor pathways are involved in experimental murine models of colitis," *Gastroenterology*, 115, 1998, pp. 1464–1475.
MacKay et al., "Mice transgenic for BAFF develop lymphocytic disorders along with autoimmune manifestations," *J Exp Med*, 190, 1999, pp. 1697–1710.
Marsters, S.A. et al. "Interaction of the TNF homologues BLYS and Apr. with the TNF receptor homologues BCMA and TACI," *Current Biology*, vol. 10, No. 13, 2000, pp. 785–788.
Moore et al., "Blys: member of the tumor necrosis factor family and B lymphocyte stimulator," *Science*, 285, 1999, pp. 260–263.
Schneider et al., "BAFF, a novel ligand of the tumor necrosis factor family, stimulates B cell growth," *J Exp Med*, 189, 1999, pp. 1747–1756.
Simonet et al., "Osteoprotegerin: a novel secreted protein involved in the regulation of bone density," *OPG*, Cell 89, 1997, pp. 309–319.
Tartaglia et al., "Identification and expression cloning of a leptin receptor, OB–R," *Cell 83*, 1995, pp. 1263–1271.
Teague et al., "Activation changes the spectrum but not the diversity of genes expressed by T cells," *Proc Natl Acad Sci USA*, 96, 1999, pp. 12691–12696.
Wong et al., "TRANCE Is a novel ligand of the tumor necrosis factor receptor family that activetes c–Jun N–terminal kinase in T cells," *J Biol Chem*, 272, 1997, pp. 25190–25194.

* cited by examiner

*Primary Examiner*—Brenda Brumback
*Assistant Examiner*—Eileen B. O'Hara
(74) *Attorney, Agent, or Firm*—Fish & Neave IP Group of Ropes & Gray LLP; James F. Haley, Jr.; Margaret A. Pierri

(57) ABSTRACT

A newly identified heteromeric ligand of the Tumor Necrosis Factor (TNF)-family, referred to as hereinafter as "APBF" has been identified.

16 Claims, 11 Drawing Sheets

A

```
                              TM
MPASSPFLLAPKGPPPQNMGGPVREPALS VALWSWGAALGAVAGAMALL T    50
QQTELQSLRREVSRLQGTGGPSQNGEGYPWQSLPEQSSDALEAWENGERS    100
                ☆
     sAPRIL
RKRRAVLTQKQKKQHSVLHLVPINATSKDDSDVTEVMWQPALRRGRGLQA    150
QGYGVRIQDAGVYLLYSQVLFQDVIFIMGQVVSREGQGRQETLFRCIRSM    200
PSHPDRAYNSCYSAGVFHLHQDILSVIIPRARAKLNLSPHGTFLGFVKL     250
```

FIG. 1a

```
SEQ. ID NO: 1

1 GGTACGAGGC TTCCTAGAGG GACTGGAACC TAATTCTCCT GAGGGTGAGG
  51 GAGGGTGGAG GGTTCAAGG GGTTCTGCAAGG CAACCGTGGC CCCACGACGG AGTGCCAGGA
 101 GCACTAACAG TACCCTTAGC TTGCTTTCCT CCTCCCTCT TTTTATTTC
 151 AAGTTCCTTT TTATTTCTCC TGCGTAACA ACCTTCTTCC CTTCTGCACC
 201 ACTGCCCGTA CCCTTACCCG CCCGCCCACC TCCTTGCTAC CCCACTCTTG
 251 AAACCACAGC TGTTGGCAGG GTCCCCAGCT CATGCCAGCC TCATCTCCTT
 301 TCTTGCTAGC CCCCAAAGGG CCTCCAGGCA ACATGGGGGG CCCAGTCAGA
 351 GAGCCGGCAC TCTCAGTTGC CCCTGTTG CTCTGCTGAC CCAACAAACA GAGCTGTGGG
 401 GGCCGTGGCT TGTGCCATGG GGACAGGAGG CAGCAGGAGG CCCTGCTGG
 451 GCCTCAGGAG AGAGGTGAGC CGGCTGCAGG GGACAGGAGG GTTCCGATGC
 501 AATGGGGAAG GGTATCCCTG GCAGAGTCTC CCGGAGCAGA GTTCGGATGC
 551 CCTGAAGCC TGGGAGAATG GGGAGAGATC CCGGAAAAGG GAGCAGTGC
 601 TCACCCAAAA ACAGAAGAAG CAGCACTCTG TCCTGCACCT GGTTCCCATT
 651 AACGCCACCT CCAAGGATGA CTCCGATGTG ACAGAGGTGA TGTGGCAACC
 701 AGCTCTTAGG CGTGGGAGAG GCCTACAGCC CCAAGGATAT GGTGTCCGAA
 751 TCCAGGATGC TGGAGTTTAT CTGCTGTATA GCCAGGTCT GTTTCAAGAC
 801 GTGACTTTCA CCATGGGTCA GGTGGTGTCT CGAGAAGGCC AAGGAAGGCA
 851 GGAGACTCTA TTCGATGTA TAAGAAGTAT GCCCTCCCAC CCGACCCGG
 901 CCTACAACAG CTGCTATAGC GCAGGTGTCT TCCATTTACA CCAAGGGAT
 951 ATTCTGAGTG TCATAATTCC CCGGGCAAGG GCGAAACTTA ACCTCTCTC
1001 ACATGGAACC TTCCTGGGGT TTGTGAAACT GTGATTGTGT TATAAAAGT
1051 GGCTCCCAGC TTGGAAGACC AGGGTGGGTA CATACTGAGA CAGCCAAGA
1101 GCTGAGTATA TAAGGAGAG GGAATGTGCA GGAACAGAGG CATCTTCCTG
1151 GGTTTGGCTC CCCGTTCCTC ACTTTCCT TTTCATTCCC ACCCCTAGA
1201 CTTTGATTTT ACGGATATCT TGCTTCTGTT CCCCATGGAG CTCCGAATTC
1251 TTGCGTGTGT GTAGATGAGG GGCGGGGGAC GGGGCGCCAGG CATTGTTCAG
1301 ACCTGGTCGG GGCCCACTGG AAGCATCCAG AACAGCACCA CCATCTTA
```

FIG. 1b

SEQ ID NO: 2

```
  1  MPASSPFLLA PKGPPGNMGG PVREPALSVA LWLSWGAALG AVACAMALLT
 51  QQTELQSLRR EVSRLQGTGG PSQNGEGYPW QSLPEQSSDA LEAWENGERS
101  RKRRAVLTQK QKKQHSVLHL VPINATSKDD SDVTEVMWQP ALRRGRGLQA
151  QGYGVRIQDA GVYLLYSQVL FQDVTFTMGQ VVSREGQGRQ ETLFRCIRSM
201  PSHPDRAYNS CYSAGVFHLH QGDILSVIIP RARAKLNLSP HGTFLGFVKL
```

FIG. 1c

SEQ ID NO: 3

```
  1  GAATTCGGCA CGAGGCTCCA GGCCACATGG GGGGCTCAGT CAGAGAGCCA
 51  GCCCTTTCGG TTGCTCTTTG GTTGAGTTGG GGGGCAGTTC TGGGGGCTGT
101  GACTTGTGCT GTCGCACTAC TGATCCAACA GACAGAGCTG CAAAGCCTAA
151  GGCGGGAGGT GAGCCGGCTG CAGCGGGCTG GAGGGCCTTC CCAGAAGCAG
201  GGAGAGCGCC CATGGCAGAG CCCTCTGGGAG CAGAGTCCTG ATGTCCTGA
251  AGCCTGGAAG GATGGGGCGA AATCTCGGAG AAGGAGAGCA GTACTCACCC
301  AGAAGCACAA GAAGAAGCAC TCAGTCCTGC ATCTTGTTCC AGTTAACATT
351  ACCTCCAAGG ACTCTGACGT GACAGAGGTG ATGTGGCAAC CAGTACTTAG
401  GCGTGGGAGA GGCCCTGGAG GCCCAGGAG ACATTGTACG AGTCTGGGAC
451  ACTGGAATTT ATCTGCTCTA TAGTCAGGTC CTGTTTCATG ATGTGACTTT
501  CACAATGGGT CAGGTGGTAT CTCGGGAAGG ACAAGGGAGA AGAGAAACTC
551  TATTCCGATG TATCAGAAGT ATGCCTTCTG ATCCTGACCG TGCCTACAAT
601  AGCTGCTACA GTGCAGTGT CTTTCATTTA CATCAAGGGG ATATTATCAC
651  TGTCAAAATT CCACGGGCAA ACGCAAAACT TAGCCTTTCT CCGCATGGAA
701  CATTCCTGGG GTTTGTGAAA CTATGATTGT TATAAAGGGG GTGGGGATTT
751  CCCATTCCAA AAACTGGCTA GACAAAGGAC AAGGAACGGT CAAGAACAGC
801  TCTCCATGGC TTTGCCTTGA CTGTTGTTCC TCCCTTTGCC TTTCCCGCTC
851  CCACTATCTG GGCTTTGACT CCATGGATAT TAAAAAAGTA GAATATTTTG
901  TGTTTATCTC CCAAAAA
```

FIG. 1d

SEQ ID NO: 4

```
  1  MGGSVREPAL SVALWLSWGA VLGAVTCAVA LLIQQTELQS LRREVSRLQR
 51  SGGPSQKQGE RPWQSLWEQS PDVLEAWKDG AKSRRRRAVL TQKHKKKHSV
101  LHLVPVNITS KDSDVTEVMW QPVLRRGRGP GGQGDIVRVW DTGIYLLYSQ
151  VLFHDVTFTM GQVVSREGQG RRETLFRCIR SMPSDPDRAY NSCYSAGVFH
201  LHQGDIITVK IPRANAKLSL SPHGTFLGFV KL
```

FIG. 1e

SEQ. ID. NO. 5

```
   1 TGCCAAGCCC TGCCATGTAG TGCACGCAGG ACATCAACAA ACACAGATAA
  51 CAGGAAATGA TCCATTCCCT GTGGTCACTT ATTCTAAAGG CCCCAACCTT
 101 CAAAGTTCAA GTAGTGATAT GGATGACTCC ACAGAAAGGG AGCAGTCACG
 151 CCTTACTTCT TGCCTTAAGA AAAGAGAAGA AATGAAACTG AAGGAGTGTG
 201 TTTCCATCCT CCCACGGAAG GAAAGCCCCT CTGTCCGATC CTCCAAGAC
 251 GGAAAGCTGC TGGCTGCAAC CTTGCTGCTG GCACTGCTGT CTTGCTGCCT
 301 CACGGTGGTG TCTTTCTACC CCTGCAAGGG GACCTGGCCA
 351 GCCTCCGGGC AGAGCTGCAG GGCCACCACG CGGAGAAGCT GCCAGCAGGA
 401 GCAGGAGCCC CCAAGGCCGG CCTGGAGGAA GCTCCAGCTG TCACCGCGGG
 451 ACTGAAAATC TTTGAACCAC CAGCTCCAGG AGAAGGCAAC TCCAGTCAGA
 501 ACAGCAGAAA TAAGCGTGCC GTTCAGGGTC CAGAAGAAAC AGTCACTCAA
 551 GACTGCTGC AACTGATTGC AGACAGTGAA CACCAACTA TACAAAAAGG
 601 ATCTTACACA TTTGTTCCAT GGCTTCTCAG CTTAAAAGG GGAAGTGCCC
 651 TAGAAGAAAA AGAGAATAAA ATATTGGTCA AGAAAACTGG TTACTTTTT
 701 ATATATGGTC AGTTTTATA TACTGATAAG ACCTACGCCA TGGACATCT
 751 AATTCAGAGG AAGAAGGTCC ATGTCTTTGG GGATGAATTG AGTCTGGTGA
 801 CTTGTTTCG ATGTATTCAA AATATGCCTG AAACACTACC CAATAATTCC
 851 TGCTATTCAG CTGGCATTGC AAAACTGGAA GAAGGAGATG AACTCCAACT
 901 TGCAATACCA AGAGAAAATG CACAAATATC ACTGGATGGA GATGTCACAT
 951 TTTTGGTGC CTGTGACCTA CTGTGACCTA CTTACACCAT GTCTGTAGCT
1001 ATTTCCTCC CTTTCTCTGT ACCCTCTAAGA AGAAAGAATC TAACTGAAAA
1051 TA
```

FIG. 2a

SEQ. ID NO. 6

```
  1  MDDSTEREQS  RLTSCLKKRE  EMKLKECVSI  LPRKESPSVR  SSKDGKLLAA
 51  TLLALLSCC   LTVVSFYQVA  ALQGDLASLR  AELQGHHAEK  LPAGAGAPKA
101  GLEEAPAVTA  GLKIFEPPAP  GEGNSSQNSR  NKRAVQGPEE  TVTQDCLQLI
151  ADSETPTIQK  GSYTFVPWLL  SFKRGSALEE  KENKILVKET  GYFFIYGQVL
201  YTDKTYAMGH  LIQRKKVHVF  GDELSLVTLF  RCIQNMPETL  PNNSCYSAGI
251  AKLEEGDELQ  LAIPRENAQI  SLDGDVTFFG  ALKLL
```

FIG. 2b

```
SEQ. ID NO.7
   1 GTGGTCACTT ACTCCAAAGG CCTAGACCTT CAAAGTGCTC CTCGTGAAT
  51 GGATGAGTCT GCAAAGACCC TGCCACCACC GTGCCTCTGT TTTTGCTCCG
 101 AGAAAGGAGA AGATATGAAA GTGGGATATG ATCCCATCAC TCCGCAGAAG
 151 GAGGAGGGTG CCTGGTTTGG GATCTGCAGG GATGAAGGC TGCTGGCTGC
 201 TACCCTCCTG CTGGCCCTGT TGTCCAGCAG TTTCACAGCG ATGTCCTTGT
 251 ACCAGTTGGC TGCCTTGCAA GCAGACCTGA TGAACCTGCG CATGGAGCTG
 301 CAGAGCTACC GAGGTTCAGC AACACCAGCC GCCGCGGGTG CTCCAGAGTT
 351 GACCGCTGA GTCAAACTCC TGACACCGGC AGCTCCTCGA CCCCACAACT
 401 CCAGCCGCGG CCACAGGAAC AGACGCGCTT TCCAGGGACC AGAGAAACA
 451 GAACAAGATG TAGACCTCTC AGCTCCTCCT GCACCATGCC TGCCTGGATG
 501 CCGCCATTCT CAACATGATG ATAATGGAAT GAACCTCAGA AACAGAACTT
 551 ACACATTTGT TCCATGGCTT CTCAGCTTTA AAAGAGGAAA TGCCTTGGAG
 601 GAGAAAGAGA ACAAATAGT GGTGAGGCAA ACAGGCTATT TCTTCATCTA
 651 CAGCCAGGTT CTATACACGG ACCCCATCTT TGCTATGGGT CATGTCATCC
 701 AGAGGAAGAA AGTACACGTC TTTGGGGACG AGCTGAGCCT GGTGACCCTG
 751 TTCCGATGTA TTCAGAATAT GCCCAAAACA CTGCCCAACA ATTCCTGCTA
 801 CTCGGCTGGC ATCGCGAGGC TGGAAGAAGG AGATGAGATT CAGCTTGCAA
 851 TTCCTCGGGA GAATGCACAG ATTTCACGCA ACGGAGACGA CACCTTCTTT
 901 GGTGCCCTAA AACTGCTGTA ACTCACTTGC TGGAGTGCGT GATCCCCTTC
 951 CCTCGTCTTC TCTGTACCTC CGAGGGAGAA ACAGACGACT GGAAAAACTA
1001 AAAGATGGGG AAAGCCGTCA GCGAAAGTTT TCTCGTGACC CGTTGAATCT
1051 GATCCAAACC AGGAAATATA ACAGACAGCC ACAACCGAAG TGTGCCATGT
1101 GAGTTATGAG AAACGGAGCC CGCGCTCAGA AAGACCGGAT GAGGAAGACC
1151 GTTTCTCCA GTCCTTTGCC AACACGCACC GCAACCTTGC TTTTTGCCTT
```

FIG. 2c

```
1201  GGGTGACACA  TGTTCAGAAT  GCAGGGAGAT  TTCCTTGTTT  TGCGATTTGC
1251  CATGAGAAGA  GGGCCCACAA  CTGCAGGTCA  CTGAAGCATT  CACGCTAAGT
1301  CTCAGGATTT  ACTCTCCCTT  CTCATGCTAA  GTACACACAC  GCTCTTTTCC
1351  AGTAACTAC   TATGGATAC   TATGGAAAGG  TTGTTTGTTT  TTAAATCTAG
1401  AAGTCTTGAA  CTGGCAATAG  ACAAAAATCC  TTATAAATTC  AAGTGTAAAA
1451  TAAACTTAAT  TAAAAAGGTT  TAAGTGTG
```

SEQ. ID NO. 8

```
  1  MDESAKTLPP  PCLCFCSEKG  EDMKVGYDPI  TPQKEEGAWF  GICRDGRLLA
 51  ATLLLALLSS  SFTAMSLYQL  AALQADLMNL  RMELQSYRGS  ATPAAAGAPE
101  LTAGVKLLTP  AAPRPHNSSR  GHRNRRAFQG  PEETEQDVDL  SAPPAPCLPG
151  CRHSQHDDNG  MNLRNRTYTF  VPWLLSFKRG  NALEEKENKI  VVRQTGYFFI
201  YSQVLYTDPI  FAMGHVIQRK  KVHVFGDELS  LVTLFRCIQN  MPKTLPNNSC
251  YSAGIARLEE  GDEIQLAIPR  ENAQISRNGD  DTFFGALKLL
```

FIG. 2d

HETEROLOGOUS POLYPEPTIDE OF THE TNF FAMILY

RELATED APPLICATIONS

This is a continuation of PCT/US01/04121, filed on Feb. 8, 2001, which claims priority from U.S. provisional application Ser. No. 60/181,670 filed on Feb. 11, 2000.

TECHNICAL FIELD

This invention relates, in part, to a newly identified heteromeric ligand of the Tumor Necrosis Factor (TNF)-family, referred to hereinafter as "APBF", its variants, derivatives, agonists and antagonists; and uses thereof. In particular, the invention relates to an APBF having a TNF-family member APRIL subunit linked non-covalently to a TNF-family member BAFF subunit.

BACKGROUND OF THE INVENTION

Tumor Necrosis Factor (TNF)-family members can best be described as master switches in the immune system controlling both cell survival and differentiation. Given the current progress in manipulating members of the TNF-family for therapeutic benefit, including anti-tumor activity as well as immune regulation and inflammation, it is likely that members of this family will provide unique means to control disease. The medical utility of the TNF ligands and antagonists to the ligands has been shown for several systems. Most notable is TNF. TNF controls a wide array of immune processes, including inducing acute inflammatory reactions, as well as maintaining lymphoid tissue homeostasis. Because of the dual role this cytokine can play in various pathological settings, both agonist and antagonist reagents have been developed as modifers of disease. For example TNF and LTα (which also signals through the TNF receptors) have been used as a treatment for cancers, especially those residing in peripheral sites, such as limb sarcomas. In this setting direct signaling by the cytokine through the receptor induces tumor cell death (Aggarwal and Natarajan, 1996. *Eur Cytokine Netw* 7:93–124). In immunological settings agents which block TNF receptor signaling (eg., anti-TNF mAb, soluble TNF-R fusion proteins) have been used to treat diseases like rheumatoid arthritis and inflammatory bowel disease. In these pathologies, TNF is acting to induce cell proliferation and effector function, thereby exacerbating autoimmune disease. In this setting blocking TNF binding to its receptor(s) has therapeutic benefit (Beutler, 1999. *J Rheumatol* 26 Suppl 57:16–21).

A more recently discovered ligand/receptor system appears amenable to similar manipulations. Lymphotoxin beta (LTβ), a TNF family member which forms heterotrimers with LTα, binds to the LTβ-R. Some adenocarcinoma tumor cells which express LTβ-R can be killed or differentiated when treated with an agonistic anti-LTβ-R mAb (Browning et al., 1996. J Exp Med 183: 867–878). In immunological settings it has been shown that anti-LTβ mAb or soluble receptor fusion protein LTβ-R-Ig can block the development of inflammatory bowel diseases, possibly by influencing dendritic cell and T cell interaction (Mackay et al., 1998. Gastroenterology 115:1464–1475).

In addition to the TNFR and LTβ-R systems, manipulation of the TRAIL (Gura, 1997. Science 277: 768) and OPG (Simonet et al. 1997. Cell 89: 309–319) pathways may be therapeutically beneficial in treating cancer and bone loss, respectively. Recently, through database searches, there has been a number of newly described members of the TNF family of ligands and receptors. In addition to the number of new members, the complexity of the ligand/receptor interactions has also increased. It is now apparent that the TNF and LT systems are not unique in the ability of the ligand to interact with more than one receptor. Among the ligands reported to bind more than one receptor or receptor decoy are FasL, TRAIL, RANKL, and LIGHT.

Thus, there is a clear need to identify and characterize additional molecules which are members of the TNF family thereby providing additional means of controlling disease and manipulating the immune system.

SUMMARY OF THE INVENTION

The present invention relates to the identification of a newly discovered heteromer in the TNF-family, APBF, its nucleotide sequences, its protein sequences and resulting polynucleotides, polypeptides as well as to its soluble form; receptor to the APBF and antibodies specific for APBF and its receptor; and uses therefrom.

The invention relates to an isolated polypeptide comprising an APRIL subunit linked via a non-covalent interaction to a BAFF subunit. In one aspect the invention is directed to an isolated polypeptide comprising an APRIL subunit selected from the group consisting of human APRIL, partial human APRIL, murine APRIL or partial murine APRIL, or amino acid substitution variants thereof; linked via non-covalent interaction to a BAFF subunit selected from the group consisting of human BAFF, partial human BAFF, murine BAFF or partial murine BAFF, or amino acid substitution variants thereof. In preferred embodiments, the partial BAFF or APRIL polypeptides are soluble portions of the polypeptides.

In preferred embodiments of the invention, the heterologous polypeptide comprises more than one APRIL subunit, and more preferably two APRIL subunits, linked non-covalently to a BAFF subunit. In alternative embodiments, the heterologous polypeptide comprises more than one BAFF subunit, and more preferably two BAFF subunits, linked non-covalently to an APRIL subunit. Thus, in preferred embodiments, the present invention is directed to heterologous polypeptide trimers of BAFF and APRIL subunits, in which the ratio of APRIL to BAFF subunits is 2:1, or alternatively 1:2.

The present invention also relates to therapeutic methods utilizing the heteromers of the invention. One aspect of the invention relates to methods of inhibiting B-cell, T-cell or tumor cell growth in an animal by administering a therapeutically effective amount of a composition selected from the group consisting of an isolated APBF molecule or active fragment thereof, a recombinant APBF molecule or active fragment thereof, and an antibody specific for APBF or an active fragment thereof. Another aspect of the invention relates to methods of stimulating B-cell or T-cell growth in an animal by administering a therapeutically effective amount of a composition selected from the group consisting of an isolated APBF molecule or active fragment thereof, a recombinant APBF molecule or active fragment thereof, and an antibody specific for APBF or an active fragment thereof.

BRIEF DESCRIPTION OF THE DRAWINGS

The following drawings depicts certain embodiments of the invention. They are illustrative only and do not limit the invention otherwise disclosed herein.

FIG. 1*a* shows the amino acid sequence of human APRIL (SEQ ID NO: 2). The predicted transmembrane region (TM, boxed), the potential N-linked glycosylation site (star) and the N-terminus of the recombinant soluble APRIL sequences are indicated. FIG. 1b shows the DNA sequence encoding human APRIL (SEQ ID NO.: 1), the amino acid sequence of human APRIL (SEQ ID NO.: 2) is shown in FIG. 1c, the DNA sequence encoding mouse APRIL (SEQ ID NO.: 3) is shown in FIG. 1d, and the amino acid sequence of mouse APRIL (SEQ ID NO.: 4) is shown in FIG. 1e.

FIG. 2a shows the DNA sequence encoding human BAFF (SEQ ID NO.: 5), the amino acid sequence of human BAFF (SEQ ID NO.: 6) is shown in FIG. 2b, the DNA sequence encoding mouse BAFF (SEQ ID NO.: 7) is shown in FIGS. 2c–2d, and the amino acid sequence of mouse BAFF (SEQ ID NO.: 8) is shown in FIG. 2d. Amino acids 1 to 46 from SEQ ID NO.: 6 represent the intracellular domain, amino acids 47 to 72 from SEQ ID NO.: 6 represent the transmembrane domain and amino acids 73 to 285 from SEQ ID NO.: 6 represent the extracellular domain.

DETAILED DESCRIPTION

Definitions

Figure 3A:
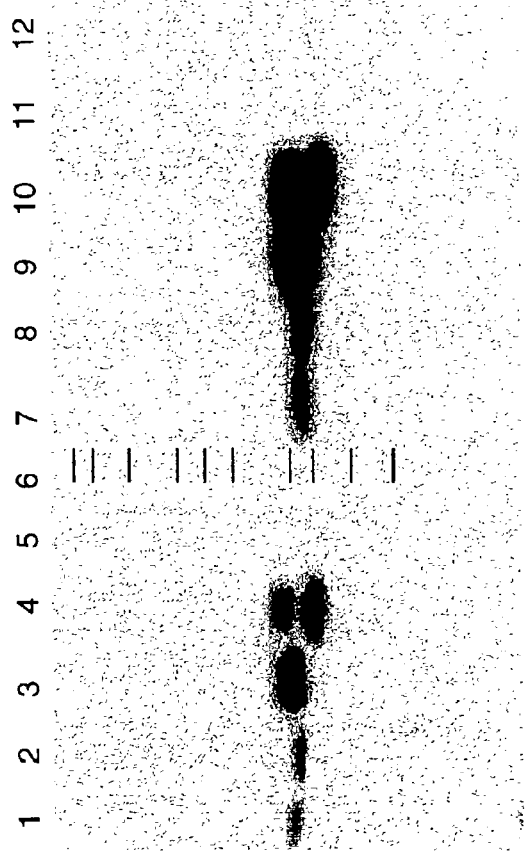
FIG. 3 shows a comparison of two western blots from cells co-transfected with various APRIL and BAFF encoding plasmids. The detection reagent used in Panel A is an anti-FLAG antibody. The detection reagent used in Panel B is an anti-BAFF antibody.

The term "APBF" or "APBF ligand" when used herein encompasses any native or recombinantly produced polypeptide having an APRIL subunit linked via a non-covalent interaction to a BAFF subunit. APBF may be isolated from a variety of sources, such as from muline or human tissue types or from other sources, or prepared by recombinant or synthetic methods. A large number of analytical biochemistry methods, known to those of skill in the art, can be utilized to determine the stoichiometry of APBF, its variants and derivatives. For example, cation exchange chromatography can be used to determine which of the various stoichiometric forms are present in the preparation derived from affinity columns. Also gel chromatography of the purified fractions will show the molecular weights of each form. The molecular weights of APRIL and BAFF are known. For example, the molecular weight of full length human BAFF, amino acids 1–285, is predicted to be 34.2 kDa for each polypeptide. The molecular weight of soluble human BAFF, amino acids A132–285, is predicted to be 18.2 kDa per polypeptide. The molecular weight of full length human APRIL, amino acids 1–250, is predicted to be 30.0 kDa for each polypeptide. The molecular weight of soluble human APRIL, amino acids A105–250, is predicted to be 17.5 kDa per polypeptide. Stoichiometric combinations contemplated in the present invention include the following formula, X APRIL: Y BAFF, where X and Y are integers greater than or equal to one. It is contemplated that the heteromer may exist as a soluble molecule, wherein all subunits are of soluble APRIL or BAFF polypeptides. It is further contemplated that the heteromer may exist as a cell associated molecule, wherein at least one of the subunits is the full length molecule containing a transmembrane domain and the other subunit(s) may contain either full length or soluble forms of APRIL or or BAFF.

The term "APRIL subunit" when used herein encompasses any native or recombinantly produced APRIL polypeptide. The APRIL subunit may be isolated from a variety of sources, such as from murine or human tissue types or from other sources, or prepared by recombinant or synthetic methods. For example, an APRIL subunit can have an amino acid sequence encoded by human APRIL (SEQ ID NO.: 1) or murine APRIL (SEQ ID NO.: 3) and variants, derivatives and unique fragments thereof. Specifically contemplated are human and murine soluble construct forms of APRIL (see above, and SEQ ID NOs.: 2 and SEQ ID NO.: 4) and variants, derivatives and unique fragments thereof.

The term "BAFF subunit" when used herein encompasses any native or recombinantly produced BAFF polypeptide. The BAFF subunit may be isolated from a variety of sources, such as from murine or human tissue types or from other sources, or prepared by recombinant or synthetic methods. For example, a BAFF subunit can have an amino acid sequence encoded by human BAFF (SEQ ID NO.: 5) or murine BAFF (SEQ ID NO.: 7) and variants, derivatives and unique fragments thereof. Specifically contemplated are human and murine soluble construct forms of BAFF (see above, and SEQ ID NO.: 6 and SEQ ID NOs.: 8) and variants, derivatives and unique fragments thereof.

As defined herein, a "unique fragment" of a protein or nucleic acid is a peptide or oligonucleotide of sufficient length to have a sequence unique to a particular gene or polypeptide, i.e., a sequence not shared by related or unrelated genes or polypeptides. Thus, for example, a unique nucleic acid fragment typically will have at least 16 nucleotide residues, and a unique polypeptide fragment typically will have at least 6 amino acid residues. Preferably, to ensure substantially unique occurrence in a typical higher eukaryotic genome, a unique nucleic acid fragment should have at least 20 nucleotide residues, and a unique polypeptide fragment should have at least 8 amino acid residues.

An "isolated" polypeptide, polynucleotide, protein, antibody, or other substance refers to a preparation of the substance devoid of at least some of the other components that may also be present where the substance or a similar substance naturally occurs or is initially obtained from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichments of the embodiments of this invention are increasingly more preferred. Thus, for example, a 2-fold enrichment is preferred, 10-fold enrichment is more preferred, 100-fold enrichment is more preferred, 1000-fold enrichment is even more preferred. A substance can also be provided in an isolated state by a process of artificial assembly, such as by chemical synthesis or recombinant expression.

"Hybridization" is the noncovalent, antiparallel bonding of complementary nucleic acid strands, in which Watson-Crick base pairing is established. To ensure specificity, hybridization should be carried out under stringent conditions, defined herein as conditions of time, temperature, probe length, probe and/or target concentration, osmotic strength, pH, detergent, carrier nucleic acid, etc. that permit no more than an occasional base-pairing mismatch within a probe/target duplex. Highly stringent conditions exclude all but about one base pair mismatch per kb of target sequence. Exemplary highly stringent conditions involve hybridization to membrane immobilized target nucleic acid at a temperature of 65° C. in the presence of 0.5 m $NaHPO_4$, 7% SDS, ImM EDTA, followed by washing at 68° C. in the presence of 0.1×SSC, 0.1% SDS. *Current Protocols in Molecular Biology* (1989), Ausubel et al., eds, Greene Publishing and Wiley Interscience, New York, N.Y. In circumstances where relatively infrequent mismatches, e.g., up to about ten mismatches per kb of target, can be tolerated, moderately stringent conditions may be used. For moderate stringency, probe/target hybrids formed under the above conditions are washed at 42° C. in the presence of 0.2×SSC, 0.1% SDS.

An "individual" is a vertebrate, preferably a mammal, more preferably a human. Mammals include, but are not limited to, farm animals, sport animals, pets, primates, mice and rats.

An "effective amount" is an amount sufficient to effect beneficial or desired clinical results. An effective amount can be administered in one or more administrations. For purposes of this invention, an effective amount is an amount of APBF, variants and derivatives of APBF and agonists and antagonists of APBF that is sufficient to ameliorate, stabilize, or delay development of a disease state associated with APBF. Particularly APBF-associated tumors. Detection and measurement of these indicators of efficacy are discussed below.

As used herein, "treatment" is an approach for obtaining beneficial or desired clinical results. For purposes of this invention, beneficial or desired clinical results include, but are not limited to, one or more of the following: alleviation of symptoms, diminishment of extent of disease, stabilized (i.e., not worsening) state of disease, preventing spread (i.e., metastasis) of disease, preventing occurrence or recurrence of disease, delay or slowing of disease progression, amelioration of the disease state, and remission (whether partial or total). Also encompassed by "treatment" is a reduction of pathological consequences of an APBF-associated tumor(s).

As used herein, the term "cancer" refers to any neoplastic disorder, including such cellular disorders as, for example, renal cell cancer, Kaposi's sarcoma, chronic leukemia, breast cancer, sarcoma, ovarian carcinoma, rectal cancer, throat cancer, melanoma, colon cancer, bladder cancer, mastocytoma, lung cancer, mammary adenocarcinoma, pharyngeal squamous cell carcinoma, and gastrointestinal or stomach cancer. Preferably, the cancer is leukemia, mastocytoma, melanoma, lymphoma, mammary adenocarcinoma, and pharyngeal squamous cell carcinoma.

To determine the "percent homology" of two amino acid sequences or of two nucleic acids, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=# of identical positions/total # of positions×100). The determination of percent homology between two sequences can be accomplished using a mathematical algorithim. A preferred, non-limiting example of a mathematical algorithim utilized for the comparison of two sequences is the algorithm of Karlin and Altschul (1990) Proc. Natl. Acad. Sci. USA 87:2264–68, modified as in Karlin and Altschul (1993) Proc. Natl. Acad. Sci. USA 90:5873–77.

The invention encompasses all nucleic acids, peptides, polynucleotides, polypeptides and proteins of the present invention that can be produced, expressed, and/or manipulated by conventional molecular engineering techniques such as the techniques set forth in *Current Protocols in Molecular Cloning*, Ausubel et al., eds. (1989), Greene Publishing and Wiley Interscience, New York, N.Y. and in Sambrook et al. (1989), *Molecular Cloning: A Laboratory Manual*, 2nd ed., Cold Spring Harbor Laboratory Press, Cold Spring Harbor, N.Y., and the teachings described and referenced in Watson et al. (1992), *Recombinant DNA* 2nd ed., Scientific American Books and W.H. Freeman & Co., New York, N.Y.

DESCRIPTION OF THE INVENTION

The present invention relates to a newly identified heteromeric member of the TNF-family, APBF, wherein APBF comprises an APRIL subunit linked non-covalently to a BAFF subunit.

APRIL, a TNF ligand known to have a role in inducing tumor cell proliferation is described in detail in PCT publications WO99/12965, WO97133 902, WO99/50416, each incorporated by reference herein. It has been shown that high levels of APRIL mRNA are detected in several tumor cell lines, as well as in colon carcinomas, metastatic lymphomas and thyroid tumors. Moreover, it has been shown that the in vitro addition of recombinant APRIL stimulates the proliferation of various cell lines. It is also recognized that in addition to inducing tumor cell proliferation that APRIL may modulate a variety of functions of the immune system cells in vitro and in vivo (Hahne et al., (1998) J. Exp. Med. 188:1185–1190).

The second component of APBF, BAFF, has been shown to have a role in inducing the proliferation of naive B cells and is described in detail in PCT publications WO98/18921, WO98/27114, and WO99/12964, each incorporated by reference herein. Like APRIL, BAFF has also been shown to modulate a variety of functions of immune system cells in vitro (Schneider et al., (1999) J. Exp. Med. 189: 1747–1756) and in vivo (Mackay et al., (1999) J. Exp. Med.190:1697–1710; Moore et al., (1999) Science.285: 260–263).

To date, all known TNF-family members, with the exception of the lymphotoxins, form homomers. It was therefore a surprising discovery, as a result of the work described herein, to identify a heteromeric polypeptide having an APRIL subunit linked non-covalently to a BAFF subunit. FIGS. 1 and 2 provides the full length and partial nucleic acid and amino acid sequences of mammalian APRIL and mammalian BAFF, respectively. The intracellular, transmembrane, and extracellular domains are identified, and a protease cleavage site is marked. N-terminal amino acid sequence analysis of APRIL secreted into the media of EBNA293 cells transfected with the full length murine APRIL cDNA plasmid identified alanine at position 87 as the first amino acid in the secreted form. Similar analysis of human BAFF overexpressed in EBNA293 cells showed that alanine at position 134 (numbering of amino acids corresponds to the naturally occuring human BAFF sequence, as found for example, in Schneider et al. 1999 J. Exp. Med 189: 1747–1756) was the first amino acid of the secreted form through amino acid 285.

In one embodiment, APBF comprises an APRIL subunit derived from a mammalian APRIL linked via a non-covalent interaction to a BAFF subunit derived from a mammalian BAFF. It is contemplated that subunits of APRIL and/or BAFF may remain cell membrane bound via their transmembrane domains, and comprise part of a membrane-bound APBF. Alternatively, the APBF may consist of the natively cleaved forms of APRIL and BAFF extracellular domains, or fragments derived from the natively cleaved forms. As illustrated in Example 1, when FLAG-tagged soluble APRIL is co-expressed with full-length BAFF, the soluble heteromeric complex is formed. This shows that the full-length BAFF is readily cleaved and complexes with the artificially generated soluble APRIL molecule. Alternatively, Example 2 demonstrates that the complex can be formed when both APRIL and BAFF are expressed as soluble molecules. This indicates that the region between the transmembrane and receptor binding domain (stalk) is not required for association. However, if one or more subunits remains uncleaved then the complex will remain tethered to the cell surface. Alternatively, the complex will be secreted. Since additional modification may take place after proteolytic cleavage from the cell surface, other subunit forms are envisioned, for example, one or more subunits may consist of a portion of the extracellular domain, as when the stalk portion (before the first beta sheet) is shortened. Also, as APRIL and BAFF contain glycosylation sites it is conceivable that one or more subunits may be aglycosylated or differentially glycosylated. Such modifications may depend on the cell in which the heteromer is expressed.

As a result of the work described herein, in which we identified APBF by co-expression and differentially tagging (see Examples 1 and 2), we are able to produce and isolate APBF by any of a number of techniques known to those of skill in the art, including for example, affinity methods, as described for example, in Example 3. Another example of a known method for isolation of proteins include ion exchange chromatography. For example, APBF may easily be separated by ion exchange chromatography based on the widely ranging pI values for soluble human APRIL (ie: hAPRIL pI=9.81) and soluble human BAFF (hBAFF pI=4.75). Heterocomplexes commonly have pI values that are additive in nature. Stoichiometrically different combinations of BAFF and APRIL proteins would be expected to bind DEAE and S-sepharose columns with significantly different affinities at a given pH. Visualization of these heterocomplexes can also be done by isoelectric focusing (IEF), followed by blotting and detection with antibodies. IEF can also be used to isolate small amounts of proteins. Since native IEF generally does not disrupt protein function it may well present itself as a useful way to assay the protein binding affinities cells and receptors and to evaluate transfections for the level of the various heteromers produced. Such methods are particularly useful in separating different subunit stoichiometries which may be present after co-transfection.

The invention further provides degenerate variant nucleic acids that encode the SEQ ID NOS.: 2, 4, 6 and 8 polypeptides or a unique fragment thereof. In yet further embodiments, the invention provides nucleic acids encoding variant APBF polypeptides, comprising amino acid sequences sharing at least 75% sequence similarity with the SEQ ID NOs.: 2, 4, 6 and/or 8. Preferably, these nucleic acids encode polypeptides sharing at least 80%, 85%, 90% or more preferably 95% amino acid sequence similarity with SEQ ID NOs.: 2, 4, 6 and/or 8. The encoded variant polypeptides comprise amino acid mutations (substitutions, deletions and/or insertions) distributed in any random or non-random frequency within SEQ ID NOs.: 2, 4, 6 and/or 8. "Similarity" as used herein refers to the sum of aligned amino acid residues that are identical to the residues of corresponding SEQ ID NOs.: 2, 4, 6 and 8 and those that are allowed point mutations therefor. Moderate gaps and/or insertions (e.g., less than about 50, preferably less than about 15, more preferably less than about 5 amino acid residues) in the aligned sequence are ignored for similarity calculation purposes. Allowed point mutations are substitutions by amino acid residues that are physically and/or functionally similar to the corresponding aligned residues of SEQ ID NOs.: 2, 4, 6 and/or 8, e.g., that have similar size, shape, hydrophilic or hydrophobic character, charge and chemical properties.

It should be understood that the present invention provides oligonucleotides that hybridize to any of the foregoing variant APBF nucleic acids, i.e., to nucleic acids that encode polypeptides comprising amino acid sequences that share at least 75% sequence similarity with SEQ ID NOs.: 2, 4, 6 and/or 8. More particularly, the invention provides oligonucleotides that hybridize to one or more unique fragments of nucleic acids encoding APBF. For therapeutic purposes and/or for PCR investigative or diagnostic purposes, the present oligonucleotides hybridize to a unique fragment comprising 5' untranslated sequence, a transcription initiation site, ORF or polypeptide coding sequence, intron-exon boundary, polyadenylation site or 3' untranslated region of the present APBF nucleic acids.

This invention also includes heteromers comprising an APRIL subunit comprising an amino acid sequence of an APRIL subunit encoded by mammalian DNA which hybridizes under high stringency conditions to a probe having the sequence of the complement of an APRIL nucleotide sequence selected from partial human APRIL cDNA (SEQ ID NO:1), human APRIL cDNA (SEQ ID NO:1), partial murine APRIL cDNA (SEQ ID NO:3) and murine APRIL cDNA (SEQ ID NO:3) or a degenerate variant of a sequence selected from partial human APRIL cDNA (SEQ ID NQ:1), human APRIL cDNA (SEQ ID NO:1), partial murine APRIL cDNA (SEQ ID NO:3) and murine APRIL cDNA (SEQTD NO:3). In such heteromers, the APRIL subunit is linked via non-covalent interaction to a BAFF subunit comprising an amino acid sequence encoded by mammalian DNA which hybridizes to a probe under high stringency conditions having the sequence of the complement of a BAFF nucleotide sequence selected from: partial human BAFF cDNA (SEQ ID NO:5), human BAFF cDNA (SEQ ID NO:5), partial murine BAFF cDNA (SEQ ID NO:7) and murine BAFF cDNA (SEQ ID NO:7) or a degenerate variant of a sequence selected from partial human BAFF cDNA (SEQ ID NO:5), human BAFF cDNA (SEQ ID NO:5), partial murine BAFF cDNA (SEQ ID NO:7) and murine BAFF cDNA (SEQ ID NO:7).

The invention also relates to heteromers formed with partial sequences of human and murine APRIL and human and murine BAFF. Preferably, these partial sequences comprise soluble forms of BAFF and APRIL. Preferred partial human APRIL molecules include amino acids A105 to L250, K110 to L250 and H115 to L250 of the full-length human APRIL sequence. Preferred partial murine APRIL molecules include amino acids A87 to L233 of the full-length murine APRIL sequence. Preferred partial human BAFF sequences include amino acids A134 to L285 and Q136 to L285 of the full-length human BAFF sequence (see, Schneider et al. 1999, J.Exp. Med. 189:1747–1756, incorporated by reference herein).

Preferred partial sequences of human and murine APRIL and BAFF also include splice variants of APRIL and BAFF. A preferred partial human APRIL sequence includes a splice variant that is the complete APRIL human sequence missing amino acids 113 to 128 (see, Kelly et al. 2000, Can. Res. 60:

1021–1027, incorporated herein by reference). Preferred partial human BAFF sequences include a splice variant which is the full-length BAFF sequence missing amino acids 142 to 160 (see, WO 00/50597). Preferred partial murine BAFF sequences include a splice variant which is full-length BAFF sequence missing amino acids 166 to 184.

The invention also encompasses soluble secreted forms of APBF. See Example 2. To create a soluble secreted form of APBF, one would use techniques known to those of skill in the art, including for example removing at the DNA level the N-terminus transmembrane regions encoding either the APRIL and/or BAFF N-terminus transmembrane regions, and some portion of the corresponding stalk region, and replace these regions with a type I leader or alternatively a type II leader sequence that will allow efficient proteolytic cleavage in the chosen expression system. A skilled artisan could vary the amount of the stalk region retained in the secretion expression construct to optimize both receptor binding properties and secretion efficiency. For example, the constructs containing all possible stalk lengths, i.e. N-terminal truncations, could be prepared such that proteins starting at amino acids 105–135, for APRIL and 134–164 for BAFF would result. The optimal length stalk sequence would result from this type of analysis.

Alternatively, APBF comprises an APRIL subunit selected from amino acid substitution variants of human APRIL, partial human APRIL, murine APRIL or partial murine APRIL linked via non-covalent interaction to a BAFF subunit selected from amino acid substitution variants of human BAFF, partial human BAFF, murine BAFF and partial murine BAFF.

Isolated APBF can be used for a number of purposes, such as the production of monoclonal or polyclonal antibodies, and identification of novel modulators affecting biological function (e.g., inhibitors), and identification of receptors interacting with APBF.

As a result of the work described herein, antibodies (polyclonal or monoclonal) specific for the identified APBF can be produced, using known methods (See, for example, *Antibodies: A Laboratory Manual* ed. by Harlow and Lane (Cold Spring Harbor Press: 1988)). Such antibodies and host cells (i.e. hybridoma cells) producing the antibodies are also the subject of the present invention.

Antibody production involves administration of one or more immunogenic doses of an APBF polypeptide preparation (whether isolated or incorporated in a cell membrane) to an appropriate non-human animal, such as a mouse, rat, rabbit, guinea pig, turkey, goat, sheep, pig, or horse. To enhance immunogenicity, the preparation can be emulsified with a conventional adjuvant, such as Freund's complete or incomplete adjuvant. Routine monitoring of serum immunoglobulins, using peripheral blood samples withdrawn at appropriate intervals (e.g., seven to ten days) after an initial or subsequent immunization, can be used to detect the onset and/or maturation of a humoral immune response. Detection and, optionally, quantitation, of immunoglobulins selectively reactive with an APBF epitope can be achieved through any conventional technique, such as ELISA, radioimmunoassay, Western blotting, or the like.

An immunoglobulin "selectively reactive with an APBF epitope" has binding specificity for the recognized epitope such that an antibody/epitope complex forms under conditions generally permissive of the formation of such complexes (e.g., under conditions of time, temperature, ionic strength, pH ionic or nonionic detergent, carrier protein, etc.). Serial dilution (titration) analysis by standard techniques is useful to estimate the avidity of antibodies in the immune serum sample for one or more epitopes unique to APBF. As defined herein, an "epitope unique to APBF" is a unique, immunogenic fragment of the full-length APBF polypeptide. A unique linear epitope typically ranges in size from about ten to about twenty-five amino acid residues, and frequently is about twelve to eighteen residues in length.

Immune serum having a high titer generally is preferred herein. Serum having a half maximal avidity for a unique APBF epitope of at least about 1:1000, preferably at least about 1:10,000, can be harvested in bulk for use as a source of polyclonal antibody useful in the detection and/or quantitation of APBF. Polyclonal immunoglobulins can, if desired, be enriched by conventional fractionation of such serum, or can be isolated by conventional immunoadsorbent techniques, e.g., using a Protein A or Protein G chromatography resin. Immune, high titer murine, rat, hamster or guinea pig serum alternatively is preferred herein for the production and screening of hybridomas secreting monoclonal antibodies selectively reactive with APBF. The present hybridomas can be produced according to well-known, standard techniques. The present monoclonal antibodies can be obtained from hybridoma culture supernatant, or from conventionally produced ascites fluid, and optionally isolated via immunoadsorbent chromatography or another suitable separation technique prior to use as agents to detect and/or quantitate APBF.

A preferred antibody, whether polyclonal or monoclonal, is selectively reactive with a unique APBF epitope that is displayed on the surface of or secreted from APBF expressing cells. The preferred antibody accordingly can be used to detect and, if desired, quantitate APBF expressing cells, e.g., normal or transformed cells in a mammalian body tissue or biopsy sample thereof. Specifically, the preferred antibody can be used to detect APBF expressing cells whether such cells are host cells or mammalian body tissue cells that aberrantly express APBF. Advantageously, intact, e.g., living, cells that display a unique APBF epitope can be detected by standard immunohistochemical, radiometric imaging or flow cytometry techniques. The present antibody can be used to detect and/or monitor APBF polypeptide production. Thus, the antibody can be used to assess the natural tissue-specific production of APBF, and thus to assess tissues likely to give rise to carcinomas or sarcomas. In addition, the present antibody can be used to monitor tumor biopsy samples to provide information relevant to selecting or revising a course of disease management, or to diagnosis, prognostication and/or staging of any disease associated with an abnormality affecting APBF. Furthermore, the present antibody can be used in a cell-sorting procedure or other cell isolation procedure to generate a substantially pure preparation of APBF expressing cells, or a cell population substantially depleted of APBF expressing cells. Each of the foregoing can be achieved through routine practice or modification of well-known techniques, including but not limited to the conjugation of a detectable moiety (e.g., a radionuclide, fluorophore, chromophore, binding pair member, or enzyme) to the APBF reactive antibody.

A hybridoma secreting an APBF reactive monoclonal antibody of the present invention additionally provides a suitable source of nucleic acid for the routine construction of a fusion polypeptide comprising an antigen-binding fragment derived from the APBF reactive antibody. The present fusion polypeptide can be prepared by routine adaptation of conventional techniques described in Deeley et al. (1996), U.S. Pat. No. 5,489,519 (incorporated herein by reference).

The fusion polypeptide can be a truncated immunoglobulin, an immunoglobulin having a desired constant region (e.g., IgG in lieu of IgM), or a "humanized" immunoglobulin having an APBF reactive Fc region fused to a framework region of human origin. Additional fusion polypeptides can comprise, in addition to an APBF reactive antigen-binding fragment, a non-immunoglobulin polypeptide such as a cytotoxic polypeptide (e.g., diphtheria toxin, ricin) or a chemoattractant polypeptide that stimulates immune effector cells (cytotoxic T cells, natural killer cells, macrophages) to kill cells that display APBF. Standard techniques well-known in the art can be used to produce appropriate immunoglobulin fusion polypeptides of the present invention.

Various forms of antibodies can also be made using standard recombinant DNA techniques. For example, humanization techniques have been developed that render non-human Mabs less antigenic in humans. Methods for humanizing Mabs by chimerisation procedures are described in EP0120694, EP0125023, EP-A-0 171496, EP-A-0173 494 and WO 86/01533, each incorporated by reference herein. Chimerisation procedures generally involve preparing antibody having the variable domains from a mouse MAb and the constant domains from a human immunoglobulin. Alternatively, methods for humanizing Mabs by CDR-grafting are described in EP-A-0239400 (Winter), WO90/07861 (Queen), WO91/09967 (CellTech), and WO91/09967 (CellTech), incorporated by reference herein. CDR-grafting generally involves grafting the complementarity determining regions (CDRs) of a mouse MAb onto the framework regions of the variable domains of a human immunoglobulin by site directed mutagenesis using long oligonucleotides. In WO91/09967, the preparation of humanized CDR-grafted antibody products which have specificity for TNF-alpha is described. In particular WO91/09967 describes in Example 5, preparation of specific humanized CDR grafted antibodies to human TNF-alpha derived from murine anti-human TNF-alpha Mabs. Using any of these known methods, therefore, antibodies specific for APBF can be produced and isolated.

The polypeptides and methods disclosed herein enable the identification of receptors which specifically interact with APBF or fragments thereof. For example, the APBF receptor can be cloned using any of the techniques known to those of skill in the art, including for example, one or more of the following approaches.

For example, one can identify an APBF receptor using expression cloning in mammalian cells. Specifically, a cDNA expression library is generated from a cell line or cell population shown to express the highest level of the receptor to the protein of interest, i.e. APBF. This approach was shown for the leptin receptor (Tartaglia et al., 1995 Cell 83: 1263–1271). The cDNA library DNA is made as pools of 2–3,000 cDNAs and transfected into an appropriate cell line which does not express the receptor. A plate assay format may be used to detect expression of the receptor on the surface of the receptor negative cell line using purified APBF. An antibody to one of the subunits or to an epitope tag is used to detect the bound protein of interest, i.e. APBF and an alkaline phosphatase conjugated secondary antibody and alkaline phosphatase substrates are used to visualize the positive cells. The plate wells are screened using a microscope. The complexity of the cDNA pools from the positive wells are reduced and then screened again. The screening continues until transfection of a single cDNA produces a positive signal. The DNA of the cDNA is sequenced and the predicted amino acid sequence analyzed for motifs and structure consistent with members of the TNF receptor family. Other expression cloning formats are available, for example, by panning on ligand coating plates, or by sorting with tagged ligand in FACS analyses.

In another approach, one can identify an APBF receptor using direct DNA sequence analysis. Specifically, a directional cDNA library is generated from a receptor positive cell line and the 5' ends sequenced using ABI automated DNA sequencing technology to determine the open reading frame. Programs to look at the cysteine residue spacing, signal and transmembrane sequences can be employed to identify potential TNF receptor family members. Full-length clones will then be isolated, expressed and examined for the ability to bind APBF. The library can also be subtracted with a APBF receptor negative cell line to reduce the complexity of the library.

In another approach, one can identify an APBF receptor by examining known or orphan receptors. Specifically, purified APBF can be used in FACS, immunoprecipitation, ELISA or Biacore assays against a panel of orphan receptors and those that have known ligands. A receptor for APBF will be positive in all of these assays.

In yet another approach, one can identify an APBF receptor using protein sequence analysis methods. Specifically, APBF can be cross-linked to the surface of cells determined to be receptor positive using standard reagents. The cross-linked complex can be immunoprecipitated using an antibody to one of the subunits or an epitope tag on the subunit. The complex can be separated on a SDS polyacrylamide, blotted to a membrane and subjected to amino acid analysis. Once amino acid sequencing reveals information about the receptor, degenerate oligonucleotide probes can be synthesized and used to screen a cDNA library made from a receptor positive cell line.

Alternatively, one can identify an APBF receptor using known biochemical approaches in combination with mass spectometry to specifically identify masses and sequences. Three illustrative examples are set forth below:

Strategy 1: Binding of [125I]-labelled APBF to different cell lines. After choosing the appropriate cell line, crosslinking of $^{125}$I-APBF to the cells followed by polyacrylamide gel electrophoresis (SDS-PAGE) and autoradiography will reveal a receptor protein that will be analyze by mass spectrometry.

Strategy 2: Crosslinking of [125I]-labelled APBF to cell lines, followed by immunoprecipitation using specific antibodies and polyacrylamide gel electrophoresis.

Strategy 3. Choosing appropriate cell lines that bind APBF. Adding purified APBF would allow the heteromer binding to the receptor. Immunoprecipitation using specific antibodies to the heteromer followed by SDS-PAGE and autoradiography will reveal specific bands that will be isolated and analyzed by mass spectrometry to identify the receptor/s.

The foregoing compositions can be used for a number of purposes, including the assessment (e.g., for diagnostic purposes) of abnormalities in the structure and/or expression of a cellular APBF gene as well as diagnosis of conditions involving abnormally high or low expression of APBF activities. For example, in WO/99/12965, it was shown that while transcript of APRIL are of low abundance in normal tissues, high levels of mRNA are detected in several tumor cells lines. The expression and growth stimulating effect of APRIL on tumor cells suggested a role for APRIL in tumorigenesis. Similarly, the monitoring of APBF transcript or polypeptide production, or gene expression level, or fluctuations therein, in one or more tumor biopsy samples is expected to provide information relevant to diagnosis, prognostication and/or staging of neoplastic disease in a cancer sufferer.

Any suitable means for detecting APBF transcript or polypeptide production or stabilization, or gene expression level, can be applied for the present diagnostic purposes. Appropriate methods are described in Sambrook et al. (1989), *Molecular Cloning: A Laboratory* Manual, 2nd ed., Cold Spring Harbor Laboratory Press, Cold Spring Harbor, N.Y.

Standard methods of analysis allow the detection of activity by cells in response to ligand binding. For example preparations of the APBF heteromer will be useful in analyses of cellular proliferation, differentiation, and apoptosis. Numerous cell types can be rapidly screened in such a manner using standard methods such as radioactive-thymidine incorporation, cell cycle analysis, and MTT uptake and conversion (detailed in Celis et al., Cell Biology, A Laboratory Handbook, Volume One, Academic Press, San Diego, Calif. (1997). Other methods of analysis that can be used to assess activity include protein phosphorylation analysis, for example, of Nuclear Factor KB transcription factor (NFκB) or c-Jun N-terminal Kinase (JNK) (eg., Mackay et al., J. Biol. Chem. 271: 24934–24938 (1996); Wong et al., J. Biol. Chem. 272: 25190–25194 (1997)). Other readily accessible assays include measurements of cytokine secretion (eg. Il-8: Chicheportiche et al., J. Biol. Chem. 272: 32401–32410 (1997)), calcium flux, pH change, cell/cell adhesion, etc (with references).

In addition to these readouts, analyses of upregulated or downregulated genes are readily done, for, by example, Northern blot, targeted array, or gene array analyses (eg. Teague et al., Proc. Natl. Acad. Sci. USA 96:12691–12696 (1999); Lockhart et al., Nat. Biotechnol. 14: 1675–1680 (1996)). Such differential gene expression studies identify specific sets of genes which respond to ligand activity, and can provide detailed profiles of ligand function (eg. Jiang et al., Oncogene 11: 1179–1189 (1995)). Particularly sensitive to such analyses are modifiers of cell growth, eg. growth hormone receptor genes, transcription factors, genes whose proteins induce or block cell death, and cell cycle mediators, among many others.

The present invention is useful for diagnosis or treatment of various immune system-related disorders in mammals, preferably humans. Such disorders include but are not limited to cancer, including, but not limited to, cellular disorders as, for example, renal cell cancer, Kaposi's sarcoma, chronic leukemia, breast cancer, sarcoma, ovarian carcinoma, rectal cancer, throat cancer, melanoma, colon cancer, bladder cancer, mastocytoma, lung cancer, mammary adenocarcinoma, pharyngeal squamous cell carcinoma, and gastrointestinal or stomach cancer. Additionally, the present invention is useful for the treatment of proliferative conditions that are not considered to be tumors, i.e. cellular hyperproliferation (hyperplasia), such as, for example, scleroderma, pannus formation in rheumatoid arthritis, postsurgical scarring and lung, liver and uterine fibrosis. In addition, the present invention is useful for the treatment of immunodeficiencies, inflammatory diseases, lymphadenopathy, autoimmune diseases, and graft versus host disease.

In one embodiment, conditions caused by a decrease in the normal level of APBF activity in an individual can be treated by administration of APBF or an agonist to APBF, where an agonist to APBF refers to any natural or synthetic composition which potentiates function, where function refers to any measurable effect of APBF interaction with cells, tissues or organisms, as measured in any known in vitro or in vivo assays, which is mediated by APBF. In one embodiment, APBF is in soluble form. The invention also provides a method of treatment of disorders caused by an increase in the normal level of APBF activity in an individual by administration of an antagonist to APBF, where an antagonist to APBF refers to any natural or synthetic composition that blocks function, where function refers to any measurable effect of APBF interaction with cells, tissues or organisms, as measured in any known in vitro or in vivo assays, which is mediated by APBF heteromers.

Pharmaceutical compositions of the invention may comprise a therapeutically effective amount of APBF, or its receptor, or fragments or mimetics thereof, and, optionally may include pharmaceutically acceptable carriers. Accordingly, this invention provides methods for treatment of cancer, and methods of stimulating, or in certain instances, inhibiting the immune system, or parts thereof by administering a pharmaceutically effective amount of a compound of the invention or its pharmaceutically acceptable salts or derivatives. In certain preferred embodiments, the invention relates to methods for inhibiting B-cell growth, T-cell growth or tumor cell growth by administering a therapeutically effective amount of an isolated APBF polypeptide or active fragment thereof, or a recombinant APBF molecule or active fragment thereof, or an antibody specific for APBF or active fragment thereof. In the context of this invention "inhibition" relates to any and all mechanisms for reducing or ameliorating activity, including inducing cell death (apoptosis). It should of course by understood that the compositions and methods of this invention can be used in combination with other therapies for various treatments.

The compositions can be formulated for a variety of routes of administration, including systemic, topical or localized administration. For systemic administration, injection is preferred, including intramuscular, intravenous, intraperitoneal, and subcutaneous for injection, the compositions of the invention can be formulated in liquid solutions, preferably in physiologically compatible buffers such as Hank's solution or Ringer's solution. In addition, the compositions may be formulated in solid form and, optionally, redissolved or suspended immediately prior to use. Lyophilized forms are also included in the invention.

The compositions can be administered orally, or by transmucosal or transdermal means. For transmucosal or transdermal administration, penetrants appropriate to the barrier to be permeated are used in the formulation. Such penetrants are known in the art, and include, for example, for transmucosal administration, bile salts, fusidic acid derivatives, and detergents. Transmucosal administration may be through nasal sprays or using suppositories. For oral administration, the compositions are formulated into conventional oral administration forms such as capsules, tablets, and tonics. For topical administration, the compositions of the invention are formulated into ointments, salves, gels, or creams as known in the art.

The dose and dosing regimen will depend on the type of disease, the patient and the patient's history. In one embodiment the disease is cancer. The amount must be effective to treat, suppress, or alter the progression of the disease. The doses may be single doses or multiple doses. If multiple doses are employed, as preferred, the frequency of administration will depend, for example, on the type of host and and type of disease, dosage amounts etc. For some types of cancers or cancer lines, daily administration will be effective, whereas for others, administration every other day or every third day will be effective. The amount of active compound administered at one time or over the course of treatment will depend on many factors. For example, the age and size of the subject, the severity and course of the disease being treated, the manner and form of administration, and the judgments of the treating physician. However, an effective dose may be in the range of from about 0.005 to about 5 mg/kg/day, preferably about 0.05 to about 0.5 mg/kg/day. The dosage amount which will be most effective will be one which results in no tumor appearance or complete regression of the tumor, and is not toxic to the patient. One skilled in the art will recognize that lower and higher doses may also be useful.

EXAMPLES

Example 1

This example describes the detection of APRIL and BAFF heteromers by immunoprecipitation following co-transfection into mammalian cells.

Methods:

The plasmids encoding FLAG-tagged human soluble APRIL, beginning with residue A105 (LT033) or K110 (PL448), soluble FLAG-tagged human TWEAK beginning at A106 (PS288) or soluble FLAG-tagged human EDA beginning at A242 (PS548) or empty vector (CH269) were co-transfected with a full-length human BAFF construct (PS544) into 293T cells using lipofectamine (Life Technologies). At 48 hrs. post-transfection, conditioned media was collected and used for immunoprecipitation experiments. The immunoprecipitation samples contained 200 µl of conditioned media, 5 µg/ml of the anti-FLAG antibody M2 (Sigma) and 800 µl of DMEM containing 10% FCS, glutamine, Pen-Strep, G418 and sodium azide and were incubated at 4° C. for 1 hour, with agitation. Then, 30 µl of ProteinA-Sepharose beads (Pharmacia) was added to the samples and the mixture was incubated overnight at 4° C. with agitation. The beads were collected by centrifugation and then washed one time with the DMEM media described above and then 3 times with PBS. The final pellet containing the beads was then suspended in 2×SDS non-reducing sample buffer and boiled for 5 minutes. The beads were spun out and 25 µl of the supernatant was loaded onto 2 separate 4–20% SDS-PAGE gradient gels (Novex). In order to examine the level of ligand expression, non-immunoprecipitated conditioned media from the co-transfected cells were also loaded. These samples were diluted two fold with 2×non-reducing sample buffer, boiled for 2 min. and then 25 µl was loaded into each lane. Each gel contained a set of immunoprecipitations and a set of non-immunoprecipitated conditioned media. After the gels were transferred to Immobilon (Millipore) filters using a BioRad apparatus, the filters were blocked in 5% non-fat dry milk diluted in TBST for 1 hr at room temperature. The filters were then separated and one was incubated with 5 µg/ml of the biotinylated anti-FLAG antibody, M2 and the other was incubated with 1 µg/ml of an anti-human BAFF antibody 53.14 (rat IgM) for about 1 hr at room temperature. The filters were washed with 3 changes of TBST and then incubated in a 1:3000 dilution of streptavidin-HRP or anti-rat IgM-HRP (Jackson ImmunoResearach) for 30 min. at room temperature. The filters were again washed 3 times and then detected using ECL reagents (Amersham). The filters were exposed to x-ray film for valious lengths of time.

Figure 3B:
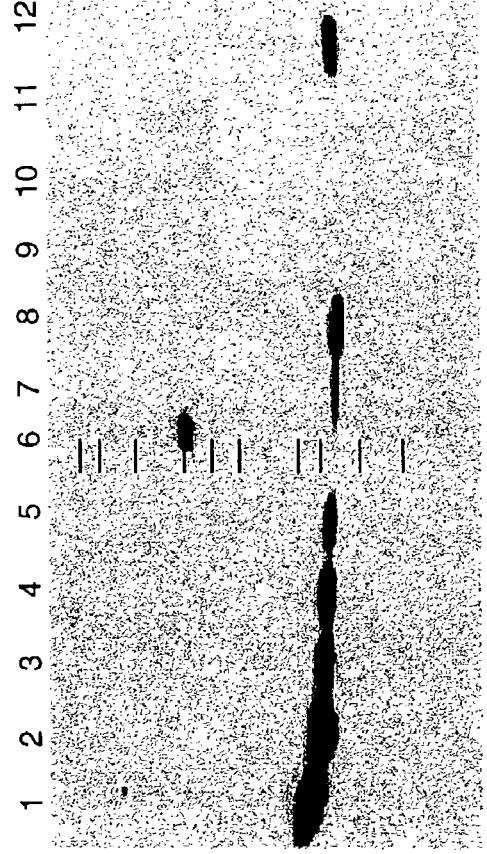

The results of the co-expression experiment are shown in FIG. 3. Panel A, lanes 1–5, show western blots of straight conditioned media from cells co-transfected with various human soluble TNF family ligands and human full length BAFF encoding plasmids. Panel A, lanes 7–12, show western blots of the straight supernatant after immunoprecipitation with an anti-FLAG antibody. The detection reagent used in Panel A is an anti-FLAG antibody. Lane 1: FLAG-tagged human soluble APRIL A105 (beginning at residue A105)+ human full length BAFF; Lane 2: FLAG-tagged human soluble APRIL K110 (beginning at residue K110)+human full length BAFF; Lane 3: FLAG-tagged human soluble TWEAK+human full length BAFF; Lane 4: FLAG-tagged human EDA+human full length BAFF; Lane 5: empty control vector; Lane 6: molecular weight standards (Benchmark, LifeTechnologies) in kDa, 185, 119, 85, 62, 51, 38.2, 26.0, 20.2, 14.5, 9.1; Lane 7–11 correspond to Lanes 1–5, respectively, after immunoprecipitation with an anti-FLAG antibody; Lane 12: purified human FLAG-BAFF Q136, 5ng.

Panel B, lanes 1–5, show western blots of straight supernatant from cells co-transfected with various APRIL and BAFF encoding plasmids. The detection reagent is an anti-BAFF antibody. Panel B, lanes 7–11 show western blots of immunoprecipitates in which cells were co-transfected with various APRIL and BAFF encoding plasmids and immunoprecipitated with an anti-FLAG antibody. The detection reagent is an anti-BAFF antibody. Lane 1: FLAG-tagged human soluble APRIL A105 (beginning at residue A105)+ human full length BAFF; Lane 2: FLAG-tagged human soluble APRIL K110 (beginning at residue K110)+human full length BAFF; Lane 3: FLAG-tagged human soluble TWEAK A106+human full length BAFF; Lane 4: FLAG-tagged human EDA A242+human full length BAFF; Lane 5: empty control vector; Lane 6: molecular weight standards (Benchmark, LifeTechnologies) in kDa, 185, 119, 85, 62, 51, 38.2, 26.0, 20.2, 14.5, 9.1; Lane 7–11 correspond to Lanes 1–5, respectively, after immunoprecipitation with an anti-FLAG antibody; Lane 12: purified human FLAG-BAFF Q136, 5 ng.

In panel A, the detection with the anti-FLAG antibody, M2 shows that all the FLAG-epitope tagged soluble ligands are expressed and secreted into the cell culture of the transfected cells. The two APRIL constructs shown in lanes 1 and 2 are expressed about 5 fold lower than TWEAK (lane 3) or EDA (lane 4). No protein is visible in lane 5, which is the control vector lane. Lanes 7–11 represent the FLAG-tagged proteins after they are immunoprecipitated. Here both APRIL proteins (lanes 7 and 8), TWEAK (lane 9) and EDA (lane 10) are precipitated and detected by M2. Lane 12 is approximately 5 ng of FLAG-BAFF for a standard.

In panel B, lanes 1–5 represent the detection of BAFF in the co-transfected cell culture media. BAFF is expressed in combination with all the FLAG-epitope tagged soluble ligands and is slightly higher in the APRIL co-transfections (lanes 1 and 2). On the right side of the blot in panel B are the M2 immunoprecipitations detected with the anti-BAFF antibody, 53.14. Here, BAFF is only immunoprecipitated in combination with APRIL (lanes 7 and 8) and not TWEAK or EDA. The standard in lane 12 indicates the size of a soluble FLAG-BAFF molecule expressed in 293T cells, which is approximately the molecular weight of the naturally cleaved molecule. This demonstrates that BAFF and APRIL form a heteromeric complex. The co-immunoprecipitations have also been evaluated in the presence of 1 M NaCl and the results are the same.

Example 2

This example describes the detection of APBF heteromers by immunoprecipitation following co-transfection of two soluble constructs into mammalian cells.

Methods:

Plasmids encoding the following human soluble TNF family ligands were constructed with the indicated N-terminal epitope tags beginning at the ligand amino acid residue indicated in a PCR3 based mammalian cell expression vector: FLAG-APRIL, beginning with residue A105 (plasmid #LT033) or H115 (plasmid #LT038), FLAG-TWEAK A106 (plasmid #PS288), myc-APRIL A105 (plasmid #JST557), and myc-BAFF Q136 (plasmid #JST556). Various constructs encoding FLAG-tagged ligands, full length murine APRIL(plasmid #LT022), or empty vector control (plasmid #CH269) were each co-transfected with the myc-BAFF Q136 construct into 293T cells using lipofectamine (Life Technologies, Gaithersburg, Md.). At 48 hrs. post-transfection, conditioned media was collected and used for immunoprecipitation experiments. The immunoprecipitation samples contained 100 µl of conditioned media, 5 µg/ml of the anti-FLAG antibody M2 (Sigma, St Louis, Mo.) and 900 µl of DMEM containing 10% FCS, glutamine, Pen-Strep, G418 and sodium azide and were incubated at 4° C. for 1 hour, with agitation. Then, 30 µl of ProteinA-Sepharose beads (Amersham Pharmacia, Piscataway, N.J.) was added to the samples and the mixture was incubated overnight at 4° C. with agitation. The beads were collected by centrifugation and then washed one time with the DMEM media described above and then 3 times with PBS. The final pellet containing the beads was then suspended in 2×SDS non-reducing sample buffer and boiled for 5 minutes. The beads were spun out and 25 µl of the supernatant was loaded onto a 4–20% SDS-PAGE gradient gel (Novex, San Diego, Calif.). After the gel was transferred to Immobilon (Millipore, Bedford, Mass.) using a BioRad apparatus, the filters were blocked in 5% non-fat dry milk diluted in TBST for 1 hr at room temperature. The filter was then incubated with 1 µg/ml of anti-myc antibody 9E10. The filter was washed with 3 changes of TBST and then incubated in a 1:3000 dilution of anti-mouse IgG-HRP (Jackson ImmunoResearch, West Grove, Pa.) for 30 min. at room temperature. The filter was again washed 3 times and then detected using ECL reagents (Amersham Pharmacia, Piscataway, N.J.). The filter was exposed to x-ray film for various lengths of time.

Figure 4:
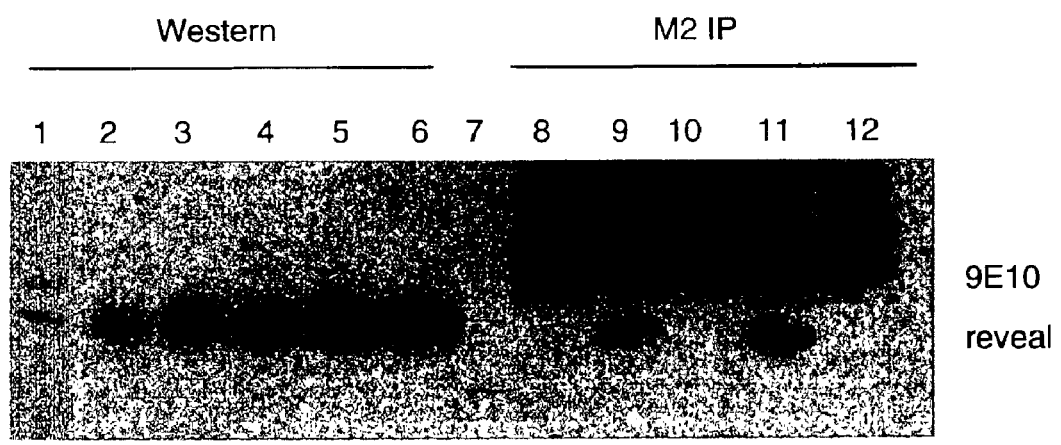
FIG. 4 shows a western blot of the immunoprecipiations of conditioned media from cells co-transfected with plasmids encoding various soluble APRIL and soluble BAFF proteins and immunoprecipitated with an anti-FLAG-tagged antibody. The detection reagent for the western blot is an anti-myc tagged antibody.

The results shown in FIG. 4 show a western blot of the immunoprecipiations of conditioned media from cells co-transfected with plasmids encoding various soluble APRIL and soluble BAFF proteins and immunoprecipitated with an anti-FLAG-tagged antibody. The detection reagent for the western blot is an anti-myc antibody, 9E10.

Lanes 1–6, show western blots of straight conditioned media from cells co-transfected with plasmids encoding various human soluble TNF family ligands and human soluble myc-BAFF Q136. Lane 7 is a molecular weight marker. Lanes 8–12, show western blots of the conditioned media after immunoprecipitation with an anti-FLAG antibody. The detection reagent used an anti-MYC antibody, 9E10. Lane 1: FLAG-tagged human soluble TWEAK A106+human soluble myc-BAFF Q136; Lane 2: FLAG-tagged human soluble APRIL H115+human soluble myc-BAFF Q136; Lane 3: MYC-tagged human soluble APRIL A105+human soluble myc-BAFF Q136; Lane 4: FLAG-tagged human soluble APRIL A105+human soluble myc-BAFF Q136; Lane 5: full length murine APRIL+human soluble myc-BAFF Q136; Lane 6: empty vector control+human soluble myc-BAFF Q136; Lane 7, molecular weight standards (Benchmark, LifeTechnologies) in kDa, 38.2, 26.0, 20.2, 14.5; Lanes 8–12 correspond to Lanes 1–5, respectively, after immunoprecipitation with an anti-FLAG antibody.

In lanes 1–6, the western blot of the conditioned media as detected by anti-MYC antibody 9E10 shows that all co-transfected 293T cells express and secrete myc-Baff Q136 into the cell culture media in nearly equal am'ts except for the FLAG-TWEAK+myc-Baff Q136 (lane 1) which shows significantly lower amounts of myc-BAFF. Lanes 8–12 show immunoprecipitation of conditioned media with anti-FLAG antibody followed by detection on western blot with anti-myc antibody 9E10. Lanes 10 and 12 show conditioned media of myc-BAFF co-transfected with myc-APRIL A105 or full length murine APRIL, respectively, and serve as negative controls in that neither APRIL construct contains the flag epitope and therefore were not immunoprecipitated by the anti-flag antibody. The FLAG-TWEAK co-transfection shows no band corresponding to myc-BAFF Q136, even upon overexposure, and therefore does not interact with MYC-BAFF. Only lanes 9 and 11, those containing myc-Baff Q136 co-expressed with FLAG-APRIL molecules H115 and A105 respectively, show the myc-baff band after anti-FLAG immunoprecipitation. Bands of approximately 18 kDa, the predicted size of myc-BAFF Q136, are observed in each lane. The intensity of the band co-expressed with FLAG-APRIL A87 (lane 3) greater than that co-expressed with FLAG-APRIL H97 (lane 4). This indicates that only soluble FLAG-APRIL ligands were able to interact with soluble MYC-BAFF to form heteromeric complexes.

This demonstrates that soluble forms of BAFF and APRIL have the ability to form a heteromeric complex, and that no cell associated form appears to be required for heteromer formation.

Example 3
Production and Isolation of APBF by Affinity Methods

Plasmids encoding the following human soluble TNF family ligands were constructed with N-terminal FLAG or 6xHis epitope tags beginning at the amino acid residue indicated in a PCR3 based mammalian cell expression vector: FLAG-APRIL, beginning with residue A87 (plasmid LT033) and RGS(H)6-BAFF Q134. These plasmids are then co-transfected into 293T cells using lipofectamine (Life Technologies, Gaithersburg, Md.) and at 48 hrs. post-transfection, conditioned media is collected. The conditioned media is dialyzed against 50 mM NaH2PO4, pH8.0; 300 mM NaCl; 10 mM imidazole and run over a Ni-NTA Superflow column (Qiagen, Valencia, Calif.). Homomers and heteromers containing the 6xHis tagged BAFF subunit bind to the Ni column; homomeric FLAG-APRIL molecules flow through. The column is washed with 50 mM NaH2PO4, pH8.0; 300 mM NaCl; 20 mM imidazole with 5–10 column volumes. The column is eluted with 5 column volumes with 50 mM NaH2PO4, pH8.0; 300 mM NaCl; 250 mM imidazole. The eluted material includes RGS(H)6-BAFF Q134 homomers and heteromers with FLAG-APRIL. This eluted material is applied to an M1 or M2 anti-FLAG Ab affinity column (Sigma, St. Louis, Mo.). A buffer exchange to 150 mM NaCl-50 mM Tris pH7.0 is performed, and the buffer adjusted to 2 mM CaCl2 if using the M1 column (this Ab requires Ca for binding). The column is washed with 150 mM NaCl-50 mM Tris pH7.0 (with 2 mM CaCl2 for M1). The M1 column is eluted by incubating the column with 150 mM NaCl-50 mM Tris pH7.0-2 mM EDTA for 30 minutes, followed by aliquots of 150 mM NaCl-50 mM Tris pH7.0-2mM EDTA, 10 min incubations, 6 times. Alternatively, both the M1 and M2 columns can be eluted by competition, with FLAG peptide by allowing the column to drain completely and eluting 5 times with one column volume each of to 150 mM NaCl-50mM Tris pH7.0 containing 100µg/ml FLAG peptide. Eluted material will contain only native FLAG-APRIL:: RGS(H)6-BAFF Q134 heteromers.

Alternatively, cell lines or cells transfected, as above, with plasmids encoding full length or untagged soluble APRIL and BAFF constructs could be used as a source to isolate APBF complexes with anti-peptide antibodies raised against regions of the extracellular domains for APRIL and BAFF. These antibodies could be coupled to a resin by conventional means. Conditioned media or cell extracts of such cells could be run first over a column containing the coupled antibody (s) against one of the ligands, for example anti-BAFF antibodiy (s). In this instance, only homomers and heteromers containing a BAFF subunit bind to the anti-BAFF column; homomeric APRIL molecules flow through. After washing the column in 150 mM NaCl-50 mM Tris pH7.0, the bound molecules could be eluted off by competition with the same BAFF peptide(s) used to raise the anti-BAFF antibody(s) by allowing the column to drain completely and eluting 5 times with one column volume each of to 150 mM NaCl-50 mM Tris pH 7.0 containing 100 μg/ml or greater the peptide(s). This eluate could be dialyzed to remove the peptide(s) and then similarly run over a column containing anti-peptide antibody(s) raised against the other ligand, in this example APRIL.). In this instance, homomeric BAFF molecules would not bind to the column and flow through. Only the remaining APBF heteromers bind to the anti-BAFF column. These APBF heteromers could be similarly eluted by competition with the same APRIL; peptide(s) used to generate the anti-APRIL antibody(s).

We claim:

1. An isolated polypeptide comprising:

(a) an APRIL subunit selected from:
 (i) human APRIL (SEQ ID NO:2) or partial human APRIL having an amino acid terminus starting at any one of amino acids 105 to 135 of human APRIL (SEQ ID NO:2);
 (ii) an amino acid substitution variant of human APRIL (SEQ ID NO:2) or partial human APRIL having an amino acid terminus starting at any one of amino acids 105 to 135 of human APRIL (SEQ ID NO:2), wherein said variant and said APRIL or partial APRIL share at least 75% sequence similarity; or
 (iii) a splice variant of human APRIL (SEQ ID NO:2), said variant missing amino acids 113 to 128 of human APRIL (SEQ ID NO:2);

(b) linked via a non-covalent interaction to a BAFF subunit selected from:
 (i) human BAFF (SEQ ID NO:6) or partial human BAFF having an amino acid terminus starting at any one of amino acids 134 to 164 of human BAFF (SEQ ID NO:6);
 (ii) an amino acid substitution variant of human BAFF (SEQ ID NO:6) or partial human BAFF having an amino acid terminus starting at any one of amino acids 134 to 164 of human BAFF (SEQ ID NO:6), wherein said variant and said BAFF or partial BAFF share at least 75% sequence similarity; or (iii) a splice variant of human BAFF (SEQ ID NO:6), said variant missing amino acids 142 to 160 of human BAFF (SEQ ID NO:6), wherein said polypeptide induces proliferation of B cells.

2. An isolated polypeptide comprising:
   (a) an APRIL subunit encoded by a DNA that hybridizes under high stringency conditions to the complement of a human APRIL cDNA comprising SEQ ID NO:1
   (b) linked via a non-covalent interaction to a BAFF subunit encoded by a DNA that hybridizes under high stringency conditions to the complement of a human BAFF cDNA comprising (SEQ ID NO:5 wherein said stringent hybridization conditions comprise hybridization at 65° C. in the presence of 0.5 M NaHPO$_4$, 7% SDS and 1 mM EDTA, followed by washing at 68° C. in the presence of 0.1×SSC and 0.1% SDS, and wherein said polypeptide induces proliferation of B cells.

3. An isolated polypeptide comprising:
   (a) an APRIL subunit selected from:
      (i) murine APRIL (SEQ ID NO:4) or partial murine APRIL having an amino acid terminus starting at amino acid 87 of murine APRIL having (SEQ ID NO:4); or
      (ii) an amino acid substitution variant of murine APRIL having (SEQ ID NO:4) or partial murine APRIL having an amino acid terminus starting at amino acid 87 of murine APRIL (SEQ ID NO:4), wherein said variant and said APRIL or partial APRIL share at least 75% sequence similarity;
   (b) linked via a non-covalent interaction to a BAFF subunit selected from:
      (i) murine BAFF having (SEQ ID NO:8);
      (ii) an amino acid substitution variant of the murine BAFF having (SEQ ID NO:8) wherein said variant and said BAFF share at least 75% sequence similarity; or
      (iii) a splice variant of murine BAFF having (SEQ ID NO:8), said variant missing amino acids 166 to 184 of murine BAFF (SEQ ID NO:8), and wherein said polypeptide induces proliferation of B cells.

4. An isolated polypeptide comprising:
   (a) an APRIL subunit encoded by a DNA that hybridizes under high stringency conditions to the complement of a murine APRIL cDNA having SEQ ID NO:3
   (b) linked via a non-covalent interaction to a BAFF subunit encoded by murine BAFF cDNA having SEQ ID NO:7 wherein said stringent hybridization conditions comprise hybridization at 65° C. in the presence of 0.5 M NaHPO$_4$, 7% SDS and 1 mM EDTA, followed by washing at 68° C. in the presence of 0.1×SSC and 0.1% SDS, and wherein said polypeptide induces proliferation of B cells.

5. A pharmaceutical composition comprising a therapeutically effective amount of the isolated polypeptide according to claim 1 or 2 and a pharmaceutically acceptable carrier.

6. The isolated polypeptide according to claims 1 or 3, wherein said sequence similarity is at least 80%.

7. The isolated polypeptide according to claims 1 or 3, wherein said sequence similarity is at least 85%.

8. The isolated polypeptide according to claims 1 or 3, wherein sequence similarity is at least 90%.

9. The isolated polypeptide according to claims 1 or 3, wherein said sequence similarity is at least 95%.

10. The isolated polypeptide according to claim 1 or 2, wherein said APRIL subunit is a partial human APRIL having an amino acid terminus starting at an amino acid selected from the group consisting of: ammo acid 105 of human APRIL (SEQ ID NO:2), amino acid 110 of human APRIL (SEQ ID NO:2) and amino acid 115 of human APRIL (SEQ ID NO:2).

11. The isolated polypeptide according to claim 1 or 2, wherein said BAFF subunit is a partial human BAFF having an amino acid terminus starting at amino acid 134 of human BAFF (SEQ ID NO:6) or amino acid 136 of human BAFF (SEQ ID NO:6).

12. The isolated polypeptide according to any one of claims 1 to 4, further comprising more than one APRIL subunit linked non-covalently to said BAFF subunit.

13. The isolated polypeptide according to claim 12, wherein two APRIL subunits are linked non-covalently to said BAFF subunit.

14. The isolated polypeptide according to any one of claims 1 to 4, further comprising more than one BAFF subunit linked non-covalently to said APRIL subunit.

15. The isolated polypeptide according to claim 13, wherein two BAFF subunits are linked non-covalently to said APRIL subunit.

16. The isolated polypeptide according to any one of claims 1 to 4, wherein said polypeptide is soluble.

* * * * *

UNITED STATES PATENT AND TRADEMARK OFFICE
CERTIFICATE OF CORRECTION

PATENT NO. : 6,875,846 B2
APPLICATION NO. : 10/214065
DATED : April 5, 2005
INVENTOR(S) : Paul Rennert et al.

It is certified that error appears in the above-identified patent and that said Letters Patent is hereby corrected as shown below:

Title Page, Item (56)

References Cited, Wong et al., change "activetes" to --activates--.

Column 31, line 12, delete "(" before "SEQ ID NO:5".

Column 31, line 23, delete "(" before "SEQ".

Column 31, line 24, delete ")" after "4".

Column 31, line 25, delete "(" before "SEQ".

Column 31, line 25, delete ")" after "4".

Column 31, line 32, delete "(" before "SEQ".

Column 31, line 32, delete ")" after "8".

Column 31, line 35, delete "(" before "SEQ".

Column 31, line 35, delete ")" after "8".

Column 31, line 38, delete "(" before "SEQ".

Column 31, line 39, delete ")" after "8".

Column 32, line 16, insert --said-- after "wherein".

Column 32, line 39, change "claim 13" to --claim 14--.

Signed and Sealed this

Tenth Day of July, 2007

JON W. DUDAS
*Director of the United States Patent and Trademark Office*

SEQUENCE LISTING

<160> NUMBER OF SEQ ID NOS: 8

<210> SEQ ID NO 1
<211> LENGTH: 1346
<212> TYPE: DNA
<213> ORGANISM: Homo sapien

<400> SEQUENCE: 1

```
ggtacgaggc ttcctagagg gactggaacc taattctcct gaggctgagg gagggtggag      60
ggtctcaagg caacgctggc cccacgacgg agtgccagga gcactaacag taccettage     120 ttgctttcct cctccctcct tttattttc aagttcctt ttatttctcc ttgcgtaaca      180
accttcttcc cttctgcacc actgcccgta cccttacccg ccccgccacc tccttgctac     240
cccactcttg aaaccacagc tgttggcagg gtccccagct catgccagcc tcatctcctt     300
tcttgctagc ccccaaaggg cctccaggca acatgggggg cccagtcaga gagccggcac     360
tctcagttgc cctctggttg agttgggggg cagctctggg ggccgtggct tgtgccatgg     420
ctctgctgac ccaacaaaca gagctgcaga gcctcaggag agaggtgagc cggctgcagg     480
ggacaggagg ccctcccaga atggggaagg gtatccctgg cagagtctcc cggagcagag     540
ttccgatgcc ctggaagcct gggagaatgg ggagagatcc cggaaaaggg agcagtgctc     600
acccaaaaac agaagaagca gcactctgtc ctgcacctgg ttcccattaa cgccacctcc     660
aaggatgact ccgatgtgac agaggtgatg tggcaaccag ctcttaggcg tgggagaggc     720
ctacaggccc aaggatatgg tgtccgaatc caggatgctg gagtttatct gctgtatagc     780
caggtcctgt ttcaagacgt gactttcacc atgggtcagg tggtgtctcg agaaggccaa     840
ggaaggcagg agactctatt ccgatgtata agaagtatgc cctcccaccc ggaccgggcc     900
tacaacagct gctatagcgc aggtgtcttc catttacacc aagggggatat tctgagtgtc     960 ataattcccc gggcaagggc gaaacttaac ctctctccac atggaacctt cctgggggtt    1020
gtgaaactgt gattgtgtta taaaagtgg ctcccagctt ggaagaccag ggtgggtaca    1080
tactggagac agccaagagc tgagtatata aaggagaggg aatgtgcagg aacagaggca    1140
tcttcctggg tttggctccc cgttcctcac tttcccttt tcattcccac ccctagact     1200 ttgattttac ggatatcttg cttctgttcc ccatggagct ccgaattctt gcgtgtgtgt    1260
agatgagggg cggggacgg gcgccaggca ttgttcagac ctggtcgggg cccactggaa    1320
gcatccagaa cagcaccacc atctta                                        1346
```

```
<210> SEQ ID NO 2
<211> LENGTH: 250
<212> TYPE: PRT
<213> ORGANISM: Homo sapien

<400> SEQUENCE: 2

Met Pro Ala Ser Ser Pro Phe Leu Leu Ala Pro Lys Gly Pro Pro Gly
1               5                   10                  15

Asn Met Gly Gly Pro Val Arg Glu Pro Ala Leu Ser Val Ala Leu Trp
            20                  25                  30

Leu Ser Trp Gly Ala Ala Leu Gly Ala Val Ala Cys Ala Met Ala Leu
        35                  40                  45

Leu Thr Gln Gln Thr Glu Leu Gln Ser Leu Arg Arg Glu Val Ser Arg
    50                  55                  60

Leu Gln Gly Thr Gly Gly Pro Ser Gln Asn Gly Glu Gly Tyr Pro Trp
65                  70                  75                  80

Gln Ser Leu Pro Glu Gln Ser Ser Asp Ala Leu Glu Ala Trp Glu Asn
                85                  90                  95

Gly Glu Arg Ser Arg Lys Arg Ala Val Leu Thr Gln Lys Gln Lys
            100                 105                 110

Lys Gln His Ser Val Leu His Leu Val Pro Ile Asn Ala Thr Ser Lys
        115                 120                 125

Asp Asp Ser Asp Val Thr Glu Val Met Trp Gln Pro Ala Leu Arg Arg
    130                 135                 140

Gly Arg Gly Leu Gln Ala Gln Gly Tyr Gly Val Arg Ile Gln Asp Ala
145                 150                 155                 160

Gly Val Tyr Leu Leu Tyr Ser Gln Val Leu Phe Gln Asp Val Asp Phe
                165                 170                 175

Thr Met Gly Gln Val Val Ser Arg Glu Gly Gln Gly Arg Gln Glu Thr
            180                 185                 190

Leu Phe Arg Cys Ile Arg Ser Met Pro Ser His Pro Asp Arg Ala Tyr
        195                 200                 205

Asn Ser Cys Tyr Ser Ala Gly Val Phe His Leu His Gln Gly Asp Ile
    210                 215                 220

Leu Ser Val Ile Ile Pro Arg Ala Arg Ala Lys Leu Asn Leu Ser Pro
225                 230                 235                 240

His Gly Thr Phe Leu Gly Phe Val Lys Leu
                245                 250

<210> SEQ ID NO 3
<211> LENGTH: 916
<212> TYPE: DNA
<213> ORGANISM: Homo sapien

<400> SEQUENCE: 3
gaattcggca gcaggctcca ggccacatgg ggggctcagt cagagagcca gcccttcgg       60 ttgctctttg gttgagttgg ggggcagttc tgggggctgt gacttgtgct gtcgcactac     120
tgatccaaca gacagagctg caaagcctaa ggcgggaggt gagccggctg cagcggagtg     180
gagggccttc ccagaagcag ggagagcgcc catggcagag cctctgggag cagagtcctg     240
atgtcctgga agcctggaag gatggggcga atctcggaga aggagagca gtactcaccc      300 agaagcacaa gaagaagcac tcagtcctgc atcttgttcc agttaacatt acctccaagg     360
actctgacgt gacagaggtg atgtggcaac cagtacttag cgtgggaga ggccctggag       420 gcccaggag acattgtacg agtctgggac actggaattt atctgctcta tagtcaggtc      480
```

```
ctgtttcatg atgtgacttt cacaatgggt caggtggtat ctcgggaagg acaaggaga     540 agagaaactc tattcgatgt atcagaagta tgccttctga tcctgaccgt gcctacaata     600
gctgctacag tgcaggtgtc tttcatttac atcaagggga tattatcact gtcaaaattc     660
cacgggcaaa cgcaaaactt agcctttctc cgcatggaac attcctgggg tttgtgaaac     720
tatgattgtt ataagggggg tggggatttc ccattccaaa aactggctag acaaaggaca     780
aggaacggtc aagaacagct ctccatggct ttgccttgac tgttgttcct cccttttgcct    840 ttcccgctcc cactatctgg gctttgactc catggatatt aaaaaagtag aatattttgt     900
gtttatctcc caaaaa                                                     916
```

<210> SEQ ID NO 4
<211> LENGTH: 232
<212> TYPE: PRT
<213> ORGANISM: Homo sapien

<400> SEQUENCE: 4

```
Met Gly Gly Ser Val Arg Glu Pro Ala Leu Ser Val Ala Leu Trp Leu
 1               5                  10                  15

Ser Trp Gly Ala Val Leu Gly Ala Val Thr Cys Ala Val Ala Leu Leu
            20                  25                  30

Ile Gln Gln Thr Glu Leu Gln Ser Leu Arg Arg Glu Val Ser Arg Leu
        35                  40                  45

Gln Arg Ser Gly Gly Pro Ser Gln Lys Gln Gly Glu Arg Pro Trp Gln
    50                  55                  60

Ser Leu Trp Glu Gln Ser Pro Asp Val Leu Glu Ala Trp Lys Asp Gly
65                  70                  75                  80

Ala Lys Ser Arg Arg Arg Arg Ala Val Leu Thr Gln Lys His Lys Lys
                85                  90                  95

Lys His Ser Val Leu His Leu Val Pro Val Asn Ile Thr Ser Lys Asp
               100                 105                 110

Ser Asp Val Thr Glu Val Met Trp Gln Pro Val Leu Arg Arg Gly Arg
            115                 120                 125

Gly Pro Gly Gly Gln Gly Asp Ile Val Arg Val Trp Asp Thr Gly Ile
       130                  135                 140

Tyr Leu Leu Tyr Ser Gln Val Leu Phe His Asp Val Thr Phe Thr Met
145                 150                 155                 160

Gly Gln Val Val Ser Arg Glu Gly Gln Gly Arg Arg Glu Thr Leu Phe
                165                 170                 175

Arg Cys Ile Arg Ser Met Pro Ser Asp Pro Asp Arg Ala Tyr Asn Ser
            180                 185                 190

Cys Tyr Ser Ala Gly Val Phe His Leu His Gln Gly Asp Ile Ile Thr
        195                 200                 205

Val Lys Ile Pro Arg Ala Asn Ala Lys Leu Ser Leu Ser Pro His Gly
    210                 215                 220

Thr Phe Leu Gly Phe Val Lys Leu
225                 230
```

<210> SEQ ID NO 5
<211> LENGTH: 1052
<212> TYPE: DNA
<213> ORGANISM: Homo sapien

<400> SEQUENCE: 5

```
tgccaagccc tgccatgtag tgcacgcagg acatcaacaa acacagataa caggaaatga      60
```

-continued

```
tccattccct gtggtcactt attctaaagg ccccaacctt caaagttcaa gtagtgatat      120
ggatgactcc acagaaaggg agcagtcacg ccttacttct tgccttaaga aaagagaaga      180
aatgaaactg aaggagtgtg tttccatcct cccacggaag gaaagcccct ctgtccgatc      240
ctccaaagac ggaaagctgc tggctgcaac cttgctgctg cactgctgt cttgctgcct       300 cacggtggtg tctttctacc aggtggccgc cctgcaaggg gacctggcca gcctccgggc      360
agagctgcag ggccaccacg cggagaagct gccagcagga gcaggagccc caaggccgg      420 cctggaggaa gctccagctg tcaccgcggg actgaaaatc tttgaaccac cagctccagg      480
agaaggcaac tccagtcaga acagcagaaa taagcgtgcc gttcagggtc agaagaaac       540 agtcactcaa gactgcttgc aactgattgc agacagtgaa acaccaacta tacaaaagg      600 atcttacaca tttgttccat ggcttctcag ctttaaaagg ggaagtgccc tagaagaaaa     660
agagaataaa atattggtca aagaaactgg ttactttttt atatatggtc aggttttata     720
tactgataag acctacgcca tgggacatct aattcagagg aagaaggtcc atgtctttgg    780
ggatgaattg agtctggtga ctttgtttcg atgtattcaa aatatgcctg aaacactacc    840
caataattcc tgctattcag ctggcattgc aaaactggaa gaaggagatg aactccaact    900
tgcaatacca agagaaaatg cacaaatatc actggatgga gatgtcacat tttttggtgc    960
attgaaactg ctgtgaccta cttacaccat gtctgtagct attttcctcc ctttctctgt   1020
acctctaaga agaaagaatc taactgaaaa ta                                  1052
```

<210> SEQ ID NO 6
<211> LENGTH: 285
<212> TYPE: PRT
<213> ORGANISM: Homo sapien

<400> SEQUENCE: 6

```
Met Asp Asp Ser Thr Glu Arg Glu Gln Ser Arg Leu Thr Ser Cys Leu
 1               5                  10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
        35                  40                  45

Ala Ala Thr Leu Leu Leu Ala Leu Leu Ser Cys Cys Leu Thr Val Val
    50                  55                  60

Ser Phe Tyr Gln Val Ala Ala Leu Gln Gly Asp Leu Ala Ser Leu Arg
65                  70                  75                  80

Ala Glu Leu Gln Gly His His Ala Glu Lys Leu Pro Ala Gly Ala Gly
                85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125

Ser Arg Asn Lys Arg Ala Val Gln Gly Pro Glu Glu Thr Val Thr Gln
    130                 135                 140

Asp Cys Leu Gln Leu Ile Ala Asp Ser Glu Thr Pro Thr Ile Gln Lys
145                 150                 155                 160

Gly Ser Tyr Thr Phe Val Pro Trp Leu Leu Ser Phe Lys Arg Gly Ser
                165                 170                 175

Ala Leu Glu Glu Lys Glu Asn Lys Ile Leu Val Lys Glu Thr Gly Tyr
            180                 185                 190

Phe Phe Ile Tyr Gly Gln Val Leu Tyr Thr Asp Lys Thr Tyr Ala Met
```

```
              195                 200                 205
        Gly His Leu Ile Gln Arg Lys Lys Val His Val Phe Gly Asp Glu Leu
            210                 215                 220

Ser Leu Val Thr Leu Phe Arg Cys Ile Gln Asn Met Pro Glu Thr Leu
        225                 230                 235                 240

Pro Asn Asn Ser Cys Tyr Ser Ala Gly Ile Ala Lys Leu Glu Glu Gly
                        245                 250                 255

Asp Glu Leu Gln Leu Ala Ile Pro Arg Glu Asn Ala Gln Ile Ser Leu
                    260                 265                 270

Asp Gly Asp Val Thr Phe Phe Gly Ala Leu Lys Leu Leu
                    275                 280                 285

<210> SEQ ID NO 7
<211> LENGTH: 1478
<212> TYPE: DNA
<213> ORGANISM: Homo sapien

<400> SEQUENCE: 7
gtggtcactt actccaaagg cctagacctt caaagtgctc ctcgtggaat ggatgagtct      60
gcaaagaccc tgccaccacc gtgcctctgt ttttgctccg agaaaggaga agatatgaaa    120
gtgggatatg atcccatcac tccgcagaag gaggagggtg cctggtttgg gatctgcagg    180
gatggaaggc tgctggctgc taccctcctg ctggccctgt tgtccagcag tttcacagcg    240
atgtccttgt accagttggc tgccttgcaa gcagacctga tgaacctgcg catggagctg    300
cagagctacc gaggttcagc aacaccagcc gccgcgggtg ctccagagtt gaccgctgga    360
gtcaaactcc tgacaccggc agctcctcga ccccacaact ccagccgcgg ccacaggaac    420
agacgcgctt ccagggacc agaggaaaca gaacaagatg tagacctctc agctcctcct    480
gcaccatgcc tgcctggatg ccgccattct caacatgatg ataatggaat gaacctcaga    540
aacagaactt acacatttgt tccatggctt ctcagcttta aaagaggaaa tgccttggag    600
gagaaagaga caaaatagt ggtgaggcaa acaggctatt tcttcatcta cagccaggtt    660
ctatacacgg accccatctt tgctatgggt catgtcatcc agaggaagaa agtacacgtc    720
tttggggacg agctgagcct ggtgaccctg ttccgatgta ttcagaatat gcccaaaaca    780
ctgcccaaca attcctgcta ctcggctggc atcgcgaggc tggaagaagg agatgagatt    840
cagcttgcaa ttcctcggga gaatgcacag atttcacgca acggagacga caccttcttt    900
ggtgccctaa aactgctgta actcacttgc tggagtgcgt gatccccttc cctcgtcttc    960
tctgtacctc cgagggagaa acagacgact ggaaaaacta aagatggggg aaagccgtca   1020
gcgaaagttt tctcgtgacc cgttgaatct gatccaaacc aggaaatata acagacagcc   1080
acaaccgaag tgtgccatgt gagttatgag aaacggagcc cgcgctcaga aagaccggat   1140
gaggaagacc gttttctcca gtcctttgcc aacacgcacc gcaaccttgc ttttgccctt   1200
gggtgacaca tgttcagaat gcagggagat tccttgtttt gcgatttgc catgagaaga   1260
gggcccacaa ctgcaggtca ctgaagcatt cacgctaagt ctcaggattt actctcccott  1320
ctcatgctaa gtacacacac gctcttttcc aggtaactac tatgggatac tatggaaagg   1380
ttgtttgttt ttaaatctag aagtcttgaa ctggcaatag acaaaaatcc ttataaattc   1440
aagtgtaaaa taaacttaat taaaaaggtt taagtgtg                          1478

<210> SEQ ID NO 8
<211> LENGTH: 290
<212> TYPE: PRT
```

-continued

<213> ORGANISM: Homo sapien

<400> SEQUENCE: 8

```
Met Asp Glu Ser Ala Lys Thr Leu Pro Pro Pro Cys Leu Cys Phe Cys
1               5                   10                  15
Ser Glu Lys Gly Glu Asp Met Lys Val Gly Tyr Asp Pro Ile Thr Pro
                20                  25                  30
Gln Lys Glu Glu Gly Ala Trp Phe Gly Ile Cys Arg Asp Gly Arg Leu
            35                  40                  45
Leu Ala Ala Thr Leu Leu Leu Ala Leu Leu Ser Ser Ser Phe Thr Ala
        50                  55                  60
Met Ser Leu Tyr Gln Leu Ala Ala Leu Gln Ala Asp Leu Met Asn Leu
65                  70                  75                  80
Arg Met Glu Leu Gln Ser Tyr Arg Gly Ser Ala Thr Pro Ala Ala Ala
                85                  90                  95
Gly Ala Pro Glu Leu Thr Ala Gly Val Lys Leu Leu Thr Pro Ala Ala
                100                 105                 110
Pro Arg Pro His Asn Ser Ser Arg Gly His Arg Asn Arg Arg Ala Phe
            115                 120                 125
Gln Gly Pro Glu Glu Thr Glu Gln Asp Val Asp Leu Ser Ala Pro Pro
        130                 135                 140
Ala Pro Cys Leu Pro Gly Cys Arg His Ser Gln His Asp Asp Asn Gly
145                 150                 155                 160
Met Asn Leu Arg Asn Arg Thr Tyr Thr Phe Val Pro Trp Leu Leu Ser
                165                 170                 175
Phe Lys Arg Gly Asn Ala Leu Glu Glu Lys Glu Asn Lys Ile Val Val
                180                 185                 190
Arg Gln Thr Gly Tyr Phe Phe Ile Tyr Ser Gln Val Leu Tyr Thr Asp
            195                 200                 205
Pro Ile Phe Ala Met Gly His Val Ile Gln Arg Lys Lys Val His Val
        210                 215                 220
Phe Gly Asp Glu Leu Ser Leu Val Thr Leu Phe Arg Cys Ile Gln Asn
225                 230                 235                 240
Met Pro Lys Thr Leu Pro Asn Asn Ser Cys Tyr Ser Ala Gly Ile Ala
                245                 250                 255
Arg Leu Glu Glu Gly Asp Glu Ile Gln Leu Ala Ile Pro Arg Glu Asn
            260                 265                 270
Ala Gln Ile Ser Arg Asn Gly Asp Asp Thr Phe Phe Gly Ala Leu Lys
        275                 280                 285
Leu Leu
    290
```